US008163914B2

(12) United States Patent
Scanio et al.

(10) Patent No.: US 8,163,914 B2
(45) Date of Patent: Apr. 24, 2012

(54) ACETAMIDE AND CARBOXAMIDE DERIVATIVES OF AZAADAMANTANE AND METHODS OF USE THEREOF

(75) Inventors: Marc J. C. Scanio, Lindenhurst, IL (US); Lei Shi, Gurnee, IL (US); William H. Bunnelle, Mundelein, IL (US); Michael R. Schrimpf, Grayslake, IL (US)

(73) Assignee: Abbott Laboratories, Abbott Park, IL (US)

( * ) Notice: Subject to any disclaimer, the term of this patent is extended or adjusted under 35 U.S.C. 154(b) by 1038 days.

(21) Appl. No.: 12/052,050

(22) Filed: Mar. 20, 2008

(65) Prior Publication Data

US 2008/0255179 A1    Oct. 16, 2008

Related U.S. Application Data

(60) Provisional application No. 60/896,749, filed on Mar. 23, 2007.

(51) Int. Cl.
C07D 471/18    (2006.01)
(52) U.S. Cl. ...................................................... 546/94
(58) Field of Classification Search .................. None
See application file for complete search history.

(56) References Cited

U.S. PATENT DOCUMENTS

| 4,816,453 | A |   | 3/1989 | Watts |
| 5,260,303 | A |   | 11/1993 | Becker et al. |
| 5,280,028 | A |   | 1/1994 | Flynn et al. |
| 5,399,562 | A |   | 3/1995 | Becker et al. |
| 5,434,151 | A |   | 7/1995 | Cai et al. |
| 5,521,193 | A | * | 5/1996 | Flynn et al. ................... 514/290 |
| 5,591,749 | A |   | 1/1997 | Becker et al. |
| 5,604,239 | A | * | 2/1997 | Becker et al. ................. 514/300 |
| 5,643,917 | A | * | 7/1997 | Flynn et al. ................... 514/290 |
| 6,468,998 | B1 |  | 10/2002 | Kuroita et al. ........... 514/214.03 |

FOREIGN PATENT DOCUMENTS

| WO | 9215593 | 9/1992 |
| WO | 9400454 | 1/1994 |
| WO | 9402482 | 2/1994 |
| WO | 9951601 | 10/1999 |
| WO | 9951602 | 10/1999 |
| WO | 0011001 | 3/2000 |

OTHER PUBLICATIONS

Richard B. Silverman, The Organic Chemistry of Drug Design & Drug Action; Chapter 2: Drug Discovery, Design, & Development, pp. 5-51, Academic Press (1992).*
Adams, E., et al., Developmental Brain Research, 139: 175-187 (2002).
Adler, E., et al., Schizophrenia Bulletin, 24(2): 189-202 (1998).
Anderson, J., et al., Journal of Pharm. and Exp. Therap., 324(1): 179-187 (2008).
Balbani, A., et al., Expert. Opin. Ther. Pat., 17(3): 287-297 (2007).
Becker, D., et al., Synthesis: 1080-1082 (1992).
Bitner, R., et al., Neuroscience, 325.6 Abstract (2006).
Broad, L., et al., Drugs of the Future, 32(2): 161-170 (2007).
Bunnelle, W., et al., Expert Opin. Ther. Patents, 13(7): 1003-1021 (2003).
Cordero-Erausquin, M., et al., PNAS, 98(5): 2803-2807 (2001).
Couturier, S., et al., Neuron, 5: 847-856 (1990).
Dajas-Bailador, F., et al., Trends in Pharm. Sciences, 25(6): 317-324 (2004).
Decker, M., et al., Expert Opin. Investig. Drugs, 10(10): 1819-1830 (2001).
De Luca, V., et al., Acta Psychiatrica Scand., 114: 211-215 (2006).
Eliel, E., et al., Stereochemistry of Organic Compounds, John Wiley and Sons Inc., New York, NY, Table of Contents (1994).
Falk, L., et al., Developmental Brain Research, 142: 151-160 (2003).
Flynn, D., et al., Bioorganic & Medicinal Chemistry Letters, 2(12): 1613-1618 (1992).
Alkondon, M., et al., Prog. Brain Res. 145: 109-120 (2004).
Friedman, J., et al., Society of Biol. Psych., 51: 349-357 (2002).
Geerts, H., Current Opinion in Invest. Drugs, 7(1): 60-69 (2006).
Gundisch, D., Expert Opin. Ther. Patents, 15(9): 1221-1239 (2005).
Gurwitz, D., Exp. Opin. Invest. Drugs, 8(6): 747-760 (1999).
Gotti, C., et al., Prog. Neurobiol., 74: 363-396 (2004).
Tsuneki, H., et al., J. Physiol., 547: 169-179 (2003).
Hogg, R., et al., Rev. Physiol. Biochem. Pharmacol., 147: 1-46 (2003).
Iriepa, I., et al., Journal of Molecular Structure, 509: 105-114 (1999).
Jonnala, R., et al., Journal of Neuroscience Research, 66: 565-572 (2001).
Keller, J., et al., Behav. Brain Research, 162: 143-152 (2005).
Kihara, T., et al., Journal of Biological Chemistry, 276: 13541-13546 (2001).
Leonard, S., et al., European Journal of Pharmacology, 393: 237-242 (2000).
Levin, E., J. Neurobiol., 53: 633-640 (2002).
Liu, Q., et al., PNAS, 98: 4734-4739 (2001).
Pabreza, L., et al., Molecular Pharmacology, 39: 9-12 (1991).
Paterson, D., et al., Progress in Neurobiology, 61: 75-111 (2000).
Prescott, D., Methods in Cell Biology, XIV: 33 et., Academic Press, New York, NY (1996).
Radek, R., et al., Psychopharmacology, 187: 47-55 (2006).
Rowley, M., et al., Journal of Medicinal Chemistry, 44(4): 477-501 (2001).
Sawa, A., et al., Molecular Medicine, pp. 3-9 (2003).
Shimohama, S., et al., Brain Research, 779: 359-363 (1988).
Stevens, K., Psychopharmacology, 136: 320-327 (1998).
Vincler, M., Expert Opin. Investig. Drugs, 14(10): 1191-1198 (2005).
Vincler, M., et al., Expert Opin. Ther. Targets, 11(7): 891-897 (2007).
Wilens, T., et al., Biol. Psychiatry, 59(11): 1065-1070 (2006).
Wilens, Timothy E. et al., Am J Psychiatry, 156(12): 1931-1937 (1999).
Greene, T. W., et al., Protecting Groups in Chemical Synthesis (3rd ed), John Wiley & Sons, NY, Table of Contents (1999).
PCT International Search Report, PCT/US2008/057643, mailing date Aug. 13, 2008.
Pasman, P., et al., Tetrahedron, 32(22): 2827-2830 (1976).

* cited by examiner

*Primary Examiner* — Janet Andres
*Assistant Examiner* — Timothy R Rozof
(74) *Attorney, Agent, or Firm* — Lisa V. Mueller; Michael Best & Friedrich LLP

(57) ABSTRACT

The invention relates to compounds that are acetamide and carboxamide derivatives of azaadamantane, compositions comprising such compounds, and methods of using such compounds and compositions.

9 Claims, No Drawings

ACETAMIDE AND CARBOXAMIDE DERIVATIVES OF AZAADAMANTANE AND METHODS OF USE THEREOF

This application claims priority from U.S. Provisional Patent Application Ser. No. 60/896,749 filed Mar. 23, 2007, which is hereby incorporated by reference in its entirety.

BACKGROUND OF THE INVENTION

1. Technical Field

The invention relates to acetamide and carboxamide derivatives of azaadamantane, compositions comprising such compounds, and methods of preventing or treating conditions and disorders using such compounds and compositions.

2. Description of Related Technology

Nicotinic acetylcholine receptors (nAChRs), belonging to the super family of ligand gated ion channels (LGIC), are widely distributed throughout the central nervous system (CNS) and the peripheral nervous system (PNS), and gate the flow of cations, controlled by acetylcholine (ACh). The nAChRs can be divided into nicotinic receptors of the muscular junction (NMJ) and neuronal nAChRs or neuronal nicotinic receptors (NNRs). The NNRs are understood to play an important role in regulating CNS function and the release of many neurotransmitters, including, but not necessarily limited to acetylcholine, norepinephrine, dopamine, serotonin and GABA. Consequently, nicotinic receptors mediate a very wide range of physiological effects, and have been targeted for therapeutic treatment of disorders relating to cognitive function, learning and memory, neurodegeneration, pain and inflammation, psychosis and sensory gating, mood and emotion, among others.

Many subtypes of NNRs exist in the CNS and periphery. Each subtype has a different effect on regulating the overall physiological function.

Typically, NNRs are ion channels that are constructed from a pentameric assembly of subunit proteins. Sixteen subunits of nAChRs have been reported to date, which are identified as $\alpha 2$-$\alpha 10$, $\beta 1$-$\beta 4$, $\gamma$, $\delta$, and $\epsilon$. Of these subunits, nine subunits, $\alpha 2$ through $\alpha 7$ and $\beta 2$ through $\beta 4$, prominently exist in the mammalian brain. Multiple functionally distinct nAChR complexes also exist, for example five $\alpha 7$ subunits can form a receptor as a homomeric functional pentamer or combinations of different subunits can complex together as in the case of $\alpha 4\beta 2$ and $\alpha 3\beta 4$ receptors (see for example, Vincler, M., McIntosh, J. M., Targeting the $\alpha 9 \alpha 10$ nicotinic acetylcholine receptor to treat severe pain, *Exp. Opin. Ther. Targets*, 2007, 11 (7): 891-897; Paterson, D. and Nordberg, A., Neuronal nicotinic receptors in the human brain, *Prog. Neurobiol.* 2000, 61: 75-111; Hogg, R. C., Raggenbass, M., Bertrand, D., Nicotinic acetylcholine receptors: from structure to brain function, *Rev. Physiol., Biochem. Pharmacol.*, 2003, 147: 1-46; Gotti, C., Clementi, F., Neuronal nicotinic receptors: from structure to pathology, *Prog. Neurobiol.*, 2004, 74: 363-396). These subunits provide for a great variety of homomeric and heteromeric combinations that account for the diverse receptor subtypes.

The NNRs, in general, are involved in various cognitive functions, such as learning, memory, attention, and therefore in CNS disorders, i.e., Alzheimer's disease (AD), Parkinson's disease (PD), attention deficit hyperactivity disorder (ADHD), Tourette's syndrome, schizophrenia, bipolar disorder, pain, and tobacco dependence (see for example, Keller, J. J., Keller, A. B., Bowers, B. J., Wehner, J. M., Performance of alpha7 nicotinic receptor null mutants is impaired in appetitive learning measured in a signaled nose poke task, *Behav. Brain Res.*, 2005, 162: 143-52; Gundish, D., Nicotinic acetylcholine receptor ligands as potential therapeutics, *Expert Opin. Ther. Patents*, 2005, 15 (9): 1221-1239; De Luca, V., Likhodi, O., Van Tol, H. H., Kennedy, J. L., Wong, A. H., Regulation of alpha7-nicotinic receptor subunit and alpha7-like gene expression in the prefrontal cortex of patients with bipolar disorder and schizophrenia, *Acta Psychiatr. Scand.*, 2006, 114: 211-5).

The homomeric $\alpha 7$ receptor is one of the most abundant nicotinic receptors, along with $\alpha 4\beta 2$ receptors, in the human brain, wherein it is heavily expressed in the hippocampus, cortex, thalamic nuclei, ventral tegmental area and substantia nigra (see for example, Broad, L. M., Sher, E., Astles, P. C., Zwart, R., O'Neill, M. J., Selective $\alpha 7$ nicotinic acetylcholine receptor ligands for the treatment of neuropsychiatric diseases, *Drugs of the Future*, 2007, 32(2): 161-170).

The role of $\alpha 7$ NNRs in neuronal signaling in the CNS also has been actively investigated (see for example, Couturier, S., Bertrand, D., Matter, J. M., Hernandez, M. C., Bertrand, S., Millar, N., Valera, S., Barkas, T., Ballivet, M., A neuronal nicotinic acetylcholine receptor subunit (alpha 7) is developmentally regulated and forms a homo-oligomeric channel blocked by alpha-BTX, *Neuron*, 1990, 5: 847-56). The $\alpha 7$ NNRs have been demonstrated to regulate interneuron excitability, modulate the release of excitatory and inhibitory neurotransmitters, and lead to neuroprotective effects in experimental in vitro models of cellular damage (see for example, Alkondon, M., Albuquerque, E. X., The nicotinic acetylcholine receptor subtypes and their function in the hippocampus and cerebral cortex, *Prog. Brain Res.*, 2004, 145: 109-20).

Biophysical studies have shown that ion channels comprised of $\alpha 7$ subunits, when expressed in heterologous expression systems, activate and desensitize rapidly, and furthermore, exhibit relatively higher calcium permeability compared to other NNR combinations (see for example, Dajas-Bailador, F., Wonnacott, S., Nicotinic acetylcholine receptors and the regulation of neuronal signaling, *Trends Pharmacol. Sci.*, 2004, 25: 317-24).

The NNR ligands have been also implicated in smoking cessation, weight control and as potential analgesics (see for example, Balbani, A. P. S., Montovani, J. C., Recent developments for smoking cessation and treatment of nicotine dependence, *Exp. Opin. Ther. Patents*, 2003, 13 (7): 287-297; Gurwitz, D., The therapeutic potential of nicotine and nicotinic agonists for weight control, *Exp. Opin. Invest. Drugs*, 1999, 8(6): 747-760; Vincler, M., Neuronal nicotinic receptors as targets for novel analgesics, *Exp. Opin. Invest. Drugs*, 2005, 14 (10): 1191-1198; Bunnelle, W. H., Decker, M. W., Neuronal nicotinic acetylcholine receptor ligands as potential analgesics, *Exp. Opin. Ther. Patents*, 2003, 13 (7): 1003-1021; Decker, M. W., Meyer, M. D., Sullivan, J. P., The therapeutic potential of nicotinic acetylcholine receptor agonists for pain control, *Exp. Opin. Invest. Drugs*, 2001, 10 (10): 1819-1830; Vincler, M., McIntosh, J. M., Targeting the $\alpha_9\alpha_{10}$ nicotinic acetylcholine receptor to treat severe pain, *Exp. Opin. Ther. Targets*, 2007, 11 (7): 891-897).

The $\alpha 7$ and $\alpha 4\beta 2$ NNRs have been shown to play a significant role in enhancing cognitive function, including aspects of learning, memory and attention (Levin, E. D., J. Neurobiol. 53: 633-640, 2002). For example, $\alpha 7$ NNRs have been linked to conditions and disorders related to attention deficit disorder, ADHD, AD, mild cognitive impairment, senile dementia, dementia associated with Lewy bodies, dementia associated with Down's syndrome, AIDS dementia, Pick's disease, as well as cognitive deficits associated with schizophrenia (CDS), among other systemic activities. The $\alpha 4\beta 2$ receptor subtype is implicated in attention, cognition, epilepsy, and pain control (Paterson, D. and Nordberg, A., Neuronal nicotinic receptors in the human brain, *Prog. Neurobiol.* 2000, 61: 75-111).

Certain compounds, like the plant alkaloid nicotine, interact with all known subtypes of the nAChRs, accounting for the profound physiological effects of this compound. Nicotine is known to provide enhanced attention and cognitive performance, reduced anxiety, enhanced sensory gating, and analgesia and neuroprotective effects when administered. Such effects are mediated by the non-selective effect of nicotine at a variety of nicotinic receptor subtypes. However, nicotine also produces adverse consequences, such as cardiovascular and gastrointestinal problems that interfere at therapeutic doses, and its addictive nature and acute toxicity are well-known. Accordingly, there is a need to identify subtype-selective compounds that evoke the beneficial effects of nicotine while eliminating or decreasing adverse effects.

The activity at the NNRs can be modified or regulated by the administration of subtype selective NNR ligands. The ligands can exhibit antagonist, agonist, or partial agonist properties and thus have potential in treatment of various cognitive disorders.

Although compounds that nonselectively demonstrate activity at a range of nicotinic receptor subtypes including the α4β2 and α7 NNRs are known, it would be beneficial to provide compounds that interact selectively with α7-containing neuronal NNRs, α4β2 NNRs, or both α7 and α4β2 NNRs compared to other subtypes.

SUMMARY OF THE INVENTION

The invention is directed to acetamide and carboxamide derivatives of azaadamantane as well as compositions comprising such compounds, and method of using the same.

One aspect of the invention relates to compounds of formula (I)

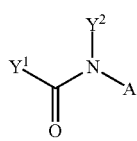

(I)

wherein
$Y^1$ is

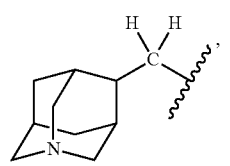

(a)

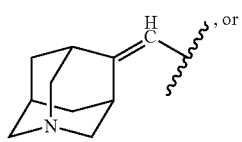

(b)

, or

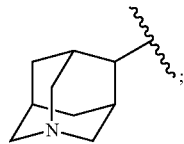

(c)

A is unsubstituted or substituted aryl, heteroaryl, heterocycle, cycloalkyl, cycloalkenyl, arylalkyl, heteroarylalkyl, heterocyclealkyl, cycloalkylalkyl, or cycloalkenylalkyl; and
$Y^2$ is hydrogen or alkyl;
or pharmaceutically acceptable salts thereof.

Another aspect of the invention relates to pharmaceutical compositions comprising compounds of the invention. Such compositions can be administered in accordance with a method of the invention, typically as part of a therapeutic regimen for treatment or prevention of conditions and disorders related to NNR activity, and more particularly α7 NNR activity, α4β2 NNR activity, or both α7 NNR activity and α4β2 NNR activity.

A further aspect of the invention relates to a method of modulating α7 NNR activity, α4β2 NNR activity, or both α7 NNR activity and α4β2 NNR activity. The method is useful for treating, preventing, or both treating and preventing conditions and disorders related to α7 NNR activity, α4β2 NNR activity, or both α7 NNR activity and α4β2 NNR activity in mammals. More particularly, the method is useful for conditions and disorders related to attention deficit disorder, ADHD, AD, Parkinson's disease, Tourette's syndrome, schizophrenia, cognitive deficits of schizophrenia (CDS), mild cognitive impairment, age-associated memory impairment (AAMI), senile dementia, AIDS dementia, Pick's disease, dementia associated with Lewy bodies, dementia associated with Down's syndrome, amyotrophic lateral sclerosis, Huntington's disease, diminished CNS function associated with traumatic brain injury, acute pain, post-surgical pain, chronic pain, inflammatory pain, neuropathic pain, smoking cessation, ischemia, sepsis, wound healing, and other complications associated with diabetes, among other systemic and neuroimmunomodulatory activities.

The compounds, compositions comprising the compounds, and methods for treating or preventing conditions and disorders by administering the compounds are further described herein.

DETAILED DESCRIPTION OF THE INVENTION

Definition of Terms

For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkyl" as used herein, means a straight or branched, saturated hydrocarbon chain containing from 1 to 10 carbon atoms, including lower alkyl, $C_{1-6}$ alkyl and $C_{1-3}$ alkyl. The term "lower alkyl" or "$C_{1-6}$ alkyl" means a straight or branched chain hydrocarbon containing 1 to 6 carbon atoms. The term "$C_{1-3}$ alkyl" means a straight or branched chain hydrocarbon containing 1 to 3 carbon atoms. Representative examples of alkyl include, but are not limited to, methyl, ethyl, n-propyl, iso-propyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" means a divalent group derived from a straight or branched chain hydrocarbon of from 1 to 10 carbon atoms. Representative examples of alkylene include, but are not limited to, —$CH_2$—, —$CH_2CH_2$—, —$CH_2CH_2CH_2$—, —$CH_2CH_2CH_2CH_2$—, and —$CH_2CH(CH_3)CH_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means phenyl, a bicyclic aryl, or a tricyclic aryl. The bicyclic aryl is naphthyl, or a phenyl fused to a monocyclic cycloalkyl, or a phenyl fused to a monocyclic cycloalkenyl. Representative examples of the bicyclic aryls include, but are not limited to, dihydroindenyl, indenyl, naphthyl, dihydronaphthalenyl, and tetrahydronaphthalenyl. The tricyclic aryl is a bicyclic aryl fused to a monocyclic cycloalkyl, or a bicyclic aryl fused to a monocyclic cycloalkenyl, or a bicyclic aryl fused to a phenyl. Representative examples of tricyclic aryl ring include, but are not limited to, anthracene, phenanthrene, dihydroanthracenyl, fluorenyl, and tetrahydrophenanthrenyl. The aryl groups of the present invention can be unsubstituted or substituted and are attached to the parent molecular moiety through any carbon atom contained within the ring systems.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, and 3-phenylpropyl.

The term "cyano" as used herein, means a —CN group.

The term "cyanoalkyl" as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkyl" or "cycloalkane" as used herein, means a monocyclic, a bicyclic, and a tricyclic cycloalkyl. The monocyclic cycloalkyl is a monocyclic carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic cycloalkyls are exemplified by a bicyclic cycloalkyl fused to a monocyclic cycloalkyl, or a bridged bicyclic cycloalkyl in which two non-adjacent carbon atoms of the bicyclic ring system are linked by an alkylene bridge of between one and four carbon atoms. Representative examples of tricyclic-ring systems include, but are not limited to, octahydro-2,5-methanopentalene (tricyclo[$3.3.1.0^{3,7}$]nonane or noradamantane), and tricyclo[$3.3.1.1^{3,7}$]decane (adamantane). The monocyclic, bicyclic, and tricyclic cycloalkyls can be unsubstituted or substituted, and are attached to the parent molecular moiety through any substitutable atom contained within the ring systems.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, and cyclohexylmethyl.

The term "cycloalkenyl" or "cycloalkene" as used herein, means a monocyclic or a bicyclic hydrocarbon ring system. The monocyclic cycloalkenyl has four, five, six, seven or eight carbon atoms and zero heteroatoms. The four-membered ring systems have one double bond, the five- or six-membered ring systems have one or two double bonds, and the seven- or eight-membered ring systems have one, two or three double bonds. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two, three, or four carbon atoms and each linking two non-adjacent carbon atoms of the ring. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl groups of the present invention can be unsubstituted or substituted, and are attached to the parent molecular moiety through any substitutable atom contained within the ring systems.

The term "cycloalkenylalkyl" as used herein, means a cycloalkenyl group, as defined herein, appended to the parent molecular moiety through an alkyl group, as defined herein.

The term "ethylenedioxy" as used herein, means a —O—$(CH_2)_2$—O— group wherein the oxygen atoms of the ethylenedioxy group are attached to two adjacent carbon atoms of a phenyl or naphthyl moiety, forming a six membered ring with the two adjacent carbon atoms of the phenyl or naphthyl moiety that it is attached to.

The term "halo" or "halogen" as used herein, means Cl, Br, I, or F.

The term "haloalkyl" as used herein, means an alkyl group, as defined herein, in which one, two, three, four, five or six hydrogen atoms are replaced by halogen. Representative examples of haloalkyl include, but are not limited to, chloromethyl, 2-fluoroethyl, trifluoromethyl, difluoromethyl, pentafluoroethyl, and 2-chloro-3-fluoropentyl.

The term "heteroaryl" as used herein, means a monocyclic heteroaryl or a bicyclic heteroaryl. The monocyclic heteroaryl is a five- or six-membered ring. The five-membered ring contains two double bonds. The five membered ring may contain one heteroatom selected from O or S; or four nitrogen atoms; or one, two, or three nitrogen atoms and optionally one oxygen or sulfur atom. The six-membered ring contains three double bonds and one, two, three or four nitrogen atoms.

Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl is exemplified by a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but not limited to, benzofuranyl, benzothienyl, benzoxazolyl, benzimidazolyl, benzoxadiazolyl, 6,7-dihydro-1,3-benzothiazolyl, imidazo[1,2-α]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, thieno[2,3-c]pyridinyl, and 5,6,7,8-tetrahydroquinolin-5-yl. The monocyclic and bicyclic heteroaryl groups of the present invention can be substituted or unsubstituted, and are connected to the parent molecular moiety through any substitutable carbon atom or any substitutable nitrogen atom contained within the ring systems.

The term "heteroarylalkyl" as used herein, means a heteroaryl, as defined herein, appended to the parent molecular moiety through an alkyl group, as defined herein.

The term "heteroatom" as used herein, means a nitrogen, oxygen, or sulfur atom.

The term "heterocycle" or "heterocyclic" as used herein, means a monocyclic, a bicyclic, or a tricyclic heterocycle ring system, provided that the heterocycle is not 1,3-benzodioxolyl, 2,3-dihydro-1,4-benzodioxine, naphtho[2,3-d][1,3]dioxole, or 2,3-dihydronaphtho[2,3-b][1,4]dioxine. The monocyclic heterocycle is a three-, four-, five-, six-, or seven-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven-membered ring contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, tetrahydropyranyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non adjacent atoms of the ring are linked by an alkylene bridge containing one, two, three, or four carbon atoms. Representative examples of bicyclic heterocycles include, but are not limited to, benzopyranyl, benzothiopyranyl, 2,3-dihydrobenzofuranyl, 2,3-dihydrobenzothienyl, and 2,3-dihydro-1H-indolyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bridged bicyclic heterocycle in which two non adjacent atoms of the bicyclic ring are linked by an alkylene bridge consisting of one, two, three, or four carbon atoms. An example of a tricyclic heterocycle is azaadmantane such as 1-azatricyclo[3.3.1.1$^{3,7}$]decane. The monocyclic, bicyclic and tricyclic heterocycles are connected to the parent molecular moiety through any substitutable carbon or nitrogen atom contained within the ring systems, and can be unsubstituted or substituted.

The term "heterocyclealkyl" as used herein, means a heterocycle, as defined herein, appended to the parent molecular moiety through an alkyl group, as defined herein.

The term "methylenedioxy" as used herein, means a —O—(CH$_2$)—O— group wherein the oxygen atoms of the methylenedioxy group are attached to two adjacent carbon atoms of the phenyl or naphthyl ring, forming a five membered ring with the two adjacent carbon atoms of the phenyl or naphthyl moiety that it is attached to.

The term "oxo" as used herein, means a =O group.

The term "parenterally," as used herein, refers to modes of administration, including intravenous, intramuscular, intraperitoneal, intrasternal, subcutaneous, intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions; as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The term "pharmaceutically acceptable salts, esters and amides" as used herein, include salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base functional group with a suitable organic acid.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, malate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate, and undecanoate.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

The term "tautomer" as used herein means a proton shift from one atom of a compound to another atom of the same compound wherein two or more structurally distinct compounds are in equilibrium with each other.

The terms "unsubstituted or substituted" with reference to aryl, cycloalkyl, cycloalkenyl, heterocycle, or heteroaryl moieties of this invention, as a substituent, or as part of a substituent, each independently, as used herein mean unsubstituted or substituted with 1, 2, 3, 4, or 5 substituents as described hereinbelow, unless otherwise noted. The optional substituents are selected from the group consisting of alkyl, alkenyl, alkynyl, halogen, cyano, oxo, methylenedioxy, ethylenedioxy, -$G^1$, —$NO_2$, —$OR^{1a}$, —$OC(O)R^{1a}$, $OC(O)N(R^b)(R^{3a})$, —$SR^{1a}$, —$S(O)_2R^{2a}$, —$S(O)_2N(R^b)(R^{3a})$, —$C(O)R^{1a}$, —$C(O)OR^{1a}$, —$C(O)N(R^b)(R^{3a})$, —$N(R^b)(R^{3a})$, —$N(R^a)C(O)R^{1a}$, —$N(R^a)S(O)_2R^{2a}$, —$N(R^a)C(O)O(R^{1a})$, —$N(R^a)C(O)N(R^b)(R^{3a})$, —$(CR^{4a}R^{5a})_m$—$NO_2$, —$(CR^{4a}R^{5a})_m OR^{1a}$, —$(CR^{4a}R^{5a})_m$—$OC(O)R^{1a}$, —$(CR^{4a}R^{5a})_m$—$OC(O)N(R^b)(R^{3a})$, —$(CR^{4a}R^{5a})_m$—$SR^{1a}$, —$(CR^{4a}R^{5a})_m$—$S(O)_2R^{2a}$, —$(CR^{4a}R^{5a})_m$—$S(O)_2N(R^b)(R^{3a})$, —$(CR^{4a}R^{5a})_m$—$C(O)R^{1a}$, —$(CR^{4a}R^{5a})_m$—$C(O)OR^{1a}$, —$(CR^{4a}R^{5a})_m$—$C(O)N(R^b)(R^{3a})$, —$(CR^{4a}R^{5a})_m$—$N(R^b)(R^{3a})$, —$(CR^{4a}R^{5a})_m$—$N(R^a)C(O)R^{1a}$, —$(CR^{4a}R^{5a})_m$—$N(R^a)S(O)_2R^{2a}$, —$(CR^{4a}R^{5a})_m$—$N(R^a)C(O)O(R^{1a})$, —$(CR^{4a}R^{5a})_m$—$N(R^a)C(O)N(R^b)(R^{3a})$, —$(CR^{4a}R^{5a})_m$-$G^1$, cyanoalkyl, and haloalkyl; wherein $R^{1a}$ and $R^{3a}$, at each occurrence, are each independently hydrogen, alkyl, haloalkyl, $G^1$, or —$(CR^6R^7)_n$-$G^1$;

$R^{2a}$, at each occurrence, is independently alkyl, haloalkyl, $G^1$, or —$(CR^6R^7)_n$-$G^1$;

$R^{4a}$, $R^{5a}$, $R^6$, and $R^7$, at each occurrence, are each independently hydrogen, alkyl, halogen, alkyl, or haloalkyl;

$R^a$ and $R^b$, at each occurrence, are each independently hydrogen, alkyl, or haloalkyl;

m and n, at each occurrence, are each independently 1, 2, 3, 4, or 5;

$G^1$ is aryl, heteroaryl, heterocycle, cycloalkyl, or cycloalkenyl, wherein each $G^1$ is independently unsubstituted or substituted with 1, 2, 3, 4 or 5 substituents selected from the group consisting of alkyl, alkenyl, alkynyl, halogen, cyano, oxo, methylenedioxy, ethylenedioxy, —$NO_2$, —$OR^{1b}$, —$OC(O)R^{1b}$, —$OC(O)N(R^b)(R^{3b})$, —$SR^{1b}$, —$S(O)_2R^b$, —$S(O)_2N(R^b)(R^{3b})$, —$C(O)R^{1b}$, —$C(O)OR^{1b}$, —$C(O)N(R^b)(R^{3b})$, —$N(R^b)(R^{3b})$, —$N(R^a)C(O)R^{1b}$, —$N(R^a)S(O)_2R^{2b}$, —$N(R^a)C(O)O(R^{1b})$, —$N(R^a)C(O)N(R^b)(R^{3b})$, —$(CR^{4b}R^{5b})_m$—$NO_2$, —$(CR^{4b}R^{5b})_m$—$OR^{1b}$, —$(CR^{4b}R^{5b})_m$—$OC(O)R^{1b}$, —$(CR^{4b}R^{5b})_m$—$OC(O)N(R^b)(R^{3b})$, —$(CR^{4b}R^{5b})_m$—$SR^{1b}$, —$(CR^{4b}R^{5b})_m$$S(O)_2R^{2b}$, —$(CR^{4b}R^{5b})_m$—$S(O)_2N(R^b)(R^{3b})$, —$(CR^{4b}R^{5b})_m$—$C(O)R^{1b}$, —$(CR^{4b}R^{5b})_m$—$C(O)OR^{1b}$, —$(CR^{4b}R^{5b})_m$—$C(O)N(R^b)(R^{3b})$, —$(CR^{4b}R^{5b})_m$—$N(R^b)(R^{3b})$, —$(CR^{4b}R^{5b})_m$—$N(R^a)C(O)R^{1b}$, —$(CR^{4b}R^{5b})_m$—$N(R^a)S(O)_2R^{2b}$, —$(CR^{4b}R^{5b})_m$—$N(R^a)C(O)O(R^{1b})$, —$(CR^{4b}R^{5b})_m$—$N(R^a)C(O)N(R^b)(R^{3b})$, cyanoalkyl, and haloalkyl;

$R^{1b}$ and $R^{3b}$, at each occurrence, are each independently hydrogen, alkyl, or haloalkyl;

$R^{2b}$, at each occurrence, is independently alkyl or haloalkyl; and $R^{4b}$ and $R^{5b}$, at each occurrence, are each independently hydrogen, halogen, alkyl, or haloalkyl.

Compounds of the Invention

In one aspect, the invention relates to compounds of formula (I),

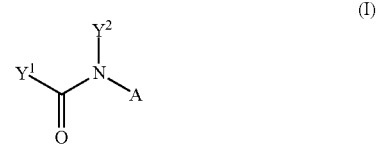

(I)

wherein
$Y^1$ is

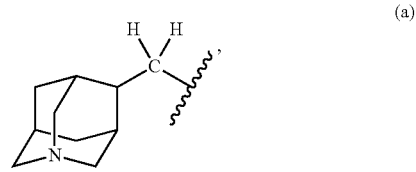

(a)

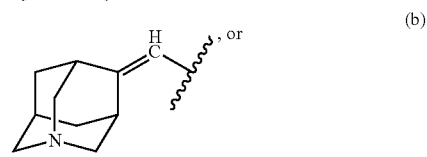

(b)

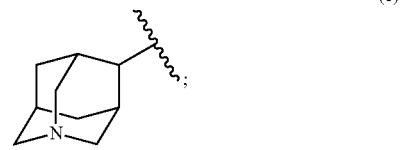

(c)

A is unsubstituted or substituted aryl, heteroaryl, heterocycle, cycloalkyl, cycloalkenyl, arylalkyl, heteroarylalkyl, heterocyclealkyl, cycloalkylalkyl, or cycloalkenylalkyl; and $Y^2$ is hydrogen or alkyl;

or pharmaceutically acceptable salts thereof.

In one embodiment, A is unsubstituted or substituted aryl, or pharmaceutically acceptable salts thereof. Particular examples of A as aryl are phenyl and naphthyl, each of which is independently unsubstituted or substituted.

In another embodiment, A is unsubstituted or substituted heteroaryl. Particular examples of A as heteroaryl are pyridinyl, quinolinyl, and isoquinolinyl, each of which is independently unsubstituted or substituted, or pharmaceutically acceptable salts thereof.

In yet another embodiment, A is arylalkyl wherein the aryl moiety of the arylalkyl is unsubstituted or substituted, or pharmaceutically acceptable salts thereof. Particular examples of A as arylalkyl are benzyl and naphthylmethyl, wherein the phenyl and the naphthyl moieties are each independently unsubstituted or substituted.

Particular examples of the optional substituents include, but are not limited to, $C_{1-6}$ alkyl (for example, methyl, ethyl, tert-butyl, and the like), halogen, $OR^{1a}$, haloalkyl (for example, trifluoromethyl, difluoromethyl, and the like), methylenedioxy, and $G^1$. For example, $R^{1a}$ is $C_{1-6}$ alkyl or haloalkyl (for example, trifluoromethyl). For example, $G^1$ is phenyl, unsubstituted or substituted.

In one embodiment, $Y^2$ is hydrogen, or pharmaceutically acceptable salts thereof.

In another embodiment, $Y^2$ is alkyl, or pharmaceutically acceptable salts thereof.

One aspect of the invention relates to compounds of formula (I), wherein $Y^1$ is formula (a), $Y^2$ is hydrogen, and A is aryl or heteroaryl, or pharmaceutically acceptable salts thereof.

Another aspect of the invention relates to compounds of formula (I), wherein $Y^1$ is formula (b), $Y^2$ is hydrogen, and A is aryl, arylalkyl or heteroaryl, or a pharmaceutically acceptable salts thereof.

Yet another aspect of the invention relates to compounds of formula (I), wherein $Y^1$ is formula (c), $Y^2$ is hydrogen, and A is aryl or heteroaryl, or a pharmaceutically acceptable salts thereof.

Exemplary compounds of formula (I) include, but are not limited to:
2-[1-azatricyclo[3.3.1.1$^{3,7}$]dec-4-ylidene]-N-(4-methylphenyl)acetamide;
2-[1-azatricyclo[3.3.1.1$^{3,7}$]dec-4-ylidene]-N-phenylacetamide;
2-[1-azatricyclo[3.3.1.1$^{3,7}$]dec-4-ylidene]-N-1-naphthylacetamide;
2-[1-azatricyclo[3.3.1.1$^{3,7}$]dec-4-ylidene]-N-(3-chlorophenyl)acetamide;
2-[1-azatricyclo[3.3.1.1$^{3,7}$]dec-4-ylidene]-N-(4-tert-butylphenyl)acetamide;
2-[1-azatricyclo[3.3.1.1$^{3,7}$]dec-4-ylidene]-N-[4-(trifluoromethoxy)phenyl]acetamide;
2-[1-azatricyclo[3.3.1.1$^{3,7}$]dec-4-ylidene]-N-[4-(trifluoromethyl)phenyl]acetamide;
2-[1-azatricyclo[3.3.1.1$^{3,7}$]dec-4-ylidene]-N-(4-chloro-1-naphthyl)acetamide;
2-[1-azatricyclo[3.3.1.1$^{3,7}$]dec-4-ylidene]-N-(4-bromophenyl)acetamide;
2-[1-azatricyclo[3.3.1.1$^{3,7}$]dec-4-ylidene]-N-pyridin-3-ylacetamide;
2-[-1-azatricyclo[3.3.1.1$^{3,7}$]dec-4-ylidene]-N-pyridin-2-ylacetamide;
2-[1-azatricyclo[3.3.1.1$^{3,7}$]dec-4-ylidene]-N-quinolin-6-ylacetamide;
2-[1-azatricyclo[3.3.1.1$^{3,7}$]dec-4-ylidene]-N-(4-chlorophenyl)acetamide;
2-[1-azatricyclo[3.3.1.1$^{3,7}$]dec-4-ylidene]-N-2-naphthylacetamide;
2-[1-azatricyclo[3.3.1.1$^{3,7}$]dec-4-ylidene]-N-(4-chlorobenzyl)acetamide;
2-[1-azatricyclo[3.3.1.1$^{3,7}$]dec-4-ylidene]-N-1,1'-biphenyl-4-ylacetamide;
2-[1-azatricyclo[3.3.1.1$^{3,7}$]dec-4-ylidene]-N-(4-fluorophenyl)acetamide;
2-[1-azatricyclo[3.3.1.1$^{3,7}$]dec-4-ylidene]-N-1,3-benzodioxol-5-ylacetamide;
2-[1-azatricyclo[3.3.1.1$^{3,7}$]dec-4-yl]-N-1-naphthylacetamide;
2-[1-azatricyclo[3.3.1.1$^{3,7}$]dec-4-yl]-N-phenylacetamide;
(4r)-N-(4-chlorophenyl)-1-azatricyclo[3.3.1.1$^{3,7}$]decane-4-carboxamide;
(4r)-N-2-naphthyl-1-azatricyclo[3.3.1.1$^{3,7}$]decane-4-carboxamide; and
(4r)-N-quinolin-6-yl-1-azatricyclo[3.3.1.1$^{3,7}$]decane-4-carboxamide;
or pharmaceutically acceptable salts thereof.

Compounds disclosed herein may contain asymmetrically substituted carbon or sulfur atoms, and accordingly may exist in, and be isolated as, single stereoisomers (e.g. single enantiomer or single diastereomer), mixtures of stereoisomers (e.g. any mixture of enantiomers or diastereomers) or racemic mixtures thereof. Individual optically-active forms of the compounds can be prepared for example, by synthesis from optically-active starting materials, by chiral synthesis, by enzymatic resolution, by biotransformation, or by chromatographic separation. It is to be understood that the present invention encompasses any racemic, optically-active, stereoisomeric form, or mixtures of various proportions thereof, which form possesses properties useful in the modulation of NNRs activity, particularly α7NNRs, α4β2, or both α7 and α4β2. Where the stereochemistry of the chiral centers present in the chemical structures illustrated herein is not specified, the chemical structure is intended to encompass compounds containing either stereoisomer of each chiral center, and mixtures thereof.

For example, compounds of formula (I), wherein $Y^1$ is formula (a) or formula (c), represent some of the stereoisomeric forms as shown below:

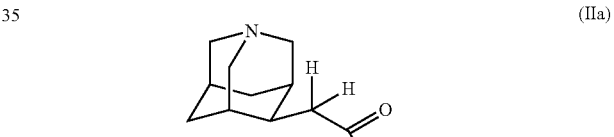

(IIa)

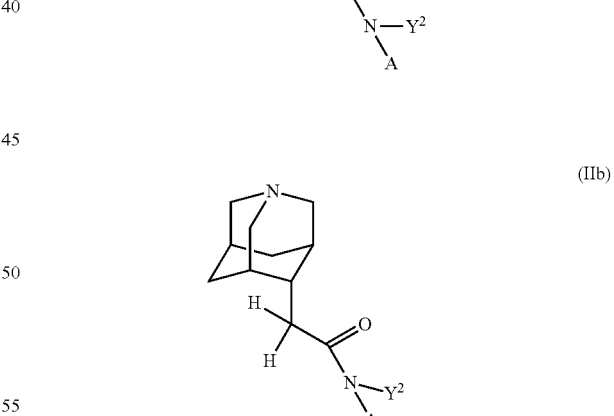

(IIb)

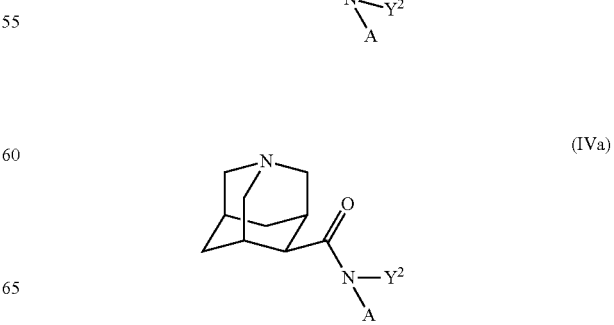

(IVa)

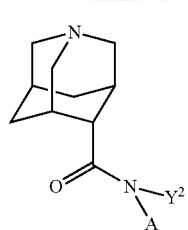

(IVb)

The azaadamantane portion of each of these isomers is not chiral, however the C-4 carbon at which the methylene of formulas (IIa) and (IIb), or the carbonyl of formulas (IVa) and (IVb) are attached is considered pseudoasymmetric. Compounds represented by formulas (IIa) and (IIb) are diastereomers. Likewise, formulas (IVa) and (IVb) are diasteromeric isomers. The configurational assignment of structures of formulas (IIa) and (IVa) are assigned 4s in accordance with that described in Synthesis, 1992, 1080, Becker, D. P.; Flynn, D. L. and as defined in Stereochemistry of Organic Compounds, E. L. Eliel, S. H Wilen; John Wiley and Sons, Inc. 1994. The configurational assignment of structures of formula (IIb) and (IVb) are assigned 4r using the same method.

Thus, it is understood that unless otherwise specified, schematic drawings of formula (I), (II), and (IV) include each possible single isomers (4r or 4s), and mixtures of both in various ratio and are useful in modulating NNRs activity.

Compounds of formula (I), wherein $Y^1$ is formula (c), can exist as formulas (IIIa) or (IIIb):

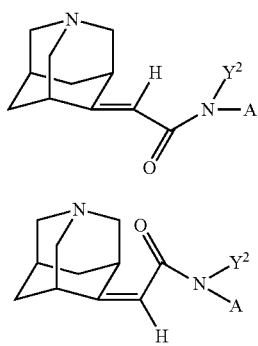

It is to be understood that formula (I) encompasses each possible single stereoisomer (formulas (IIIa) or (IIIb)) and mixtures thereof, unless otherwise specified.

Geometric isomers can exist in the present compounds. The invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or heterocyclealkyl are designated as being of cis or trans configuration.

It is to be understood that compounds disclosed herein may exhibit the phenomenon of tautomerism.

The compounds within this specification may be represented by only one of the possible tautomeric, geometric or stereoisomeric forms in the formulae and names. However, the invention encompasses any possible tautomeric, geometric or stereoisomeric forms, and mixtures thereof, and is not to be limited merely to any one tautomeric, geometric or stereoisomeric form utilized within the naming of the compounds or formulae drawings.

Compositions of the Invention

The invention also provides pharmaceutical compositions comprising of compounds of the invention, or pharmaceutically acceptable salts thereof, formulated together with one or more pharmaceutically acceptable carriers.

The compounds identified by the methods described hereinabove may be administered as the sole pharmaceutical agent or in combination with one or more other pharmaceutical agents where the combination causes no unacceptable adverse effects. For example, the compounds of this invention can be combined with an atypical antipsychotic. Specific examples of suitable atypical antipsychotics include, but are not limited to, clozapine, risperidone, olanzapine, quietapine, ziprasidone, zotepine, iloperidone, and the like. Thus, the present invention also includes pharmaceutical compositions which are comprised of therapeutically effective amount of compounds identified by the methods described herein, or pharmaceutically acceptable salts thereof, one or more pharmaceutical agents as disclosed hereinabove, and one or more pharmaceutically acceptable carriers.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The pharmaceutical compositions can be formulated for oral administration in solid, semi-solid or liquid form.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that releases the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The compounds of the invention can be used in the form of pharmaceutically acceptable salts derived from inorganic or organic acids.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulfuric acid and phosphoric acid and such organic acids as benzenesulfonic acid, citric acid, gluconic acid, maleic acid, oxalic acid, and succinic acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, and piperazine.

The invention also contemplates pharmaceutically acceptable compounds that when administered to a patient in need thereof may be converted through in vivo biotransformation into compounds of formula (I).

Methods of the Invention

Compounds and compositions of the invention are useful for modulating the effects of NNRs, and more particularly α7 NNRs, α4β2 NNRs, or both α7 and α4β2 NNRs. In particular, the compounds and compositions of the invention can be used for treating or preventing disorders modulated by α7 NNRs, or α4β2 NNRs, or both α7 and α4β2 NNRs. Typically, such disorders can be ameliorated by selectively modulating the α4β2 NNRs, α4β2 NNRs, or both α7 and α4β2 NNRs in a mammal, preferably by administering a compound or composition of the invention, either alone or in combination with one or more additional pharmaceutical agents, for example, as part of a therapeutic regimen.

Compounds for the method of the invention, including but not limited to those specified in the examples or otherwise specifically named, can modulate, and often possess an affinity for, NNRs, and more particularly α7 NNRs, α4β2 NNRs, or both α7 and α4β2 NNRs. As α7 NNRs, α4β2 NNRs, or both α7 and α4β2 NNRs ligands, the compounds of the invention can be useful for the treatment or prevention of a number of α7 NNR, α4β2 NNR, or both α7 and α4β2 NNR mediated diseases or conditions.

Specific examples of compounds that can be useful for the treatment or prevention of α7 NNRs, α4β2 NNRs, or both α7 and α4β2 NNRs mediated diseases or conditions include, but are not limited to, compounds described in the Compounds of the Invention and also in the Examples.

Methods for preparing compounds useful in the method of the invention also can be found in Iriepa, I, et al. J. Molec. Struct. 1999, 509, 105; Flynn, D. L., et al. Bioorg. Med. Chem. Lett. 1992, 2, 1613; U.S. Pat. No. 4,816,453; WO 94/00454; U.S. Pat. No. 5,280,028; U.S. Pat. No. 5,399,562; WO 92/15593; U.S. Pat. No. 5,260,303; U.S. Pat. No. 5,591,749;U.S. Pat. No. 5,434,151; and U.S. Pat. No. 5,604,239.

For example, α7 NNRs have been shown to play a significant role in enhancing cognitive function, including aspects of learning, memory and attention (Levin, E. D., J. Neurobiol. 53: 633-640, 2002). As such, α7 ligands are suitable for the treatment of conditions and disorders related to memory and/or cognition including, for example, attention deficit disorder, ADHD, AD, mild cognitive impairment, senile dementia, AIDS dementia, Pick's disease, dementia associated with Lewy bodies, and dementia associated with Down's syndrome, as well as CDS.

In addition, α7-containing NNRs have been shown to be involved in the cytoprotective effects of nicotine both in vitro (Jonnala, R. B. and Buccafusco, J. J., J. Neurosci. Res. 66: 565-572, 2001) and in vivo (Shimohama, S. et al., Brain Res. 779: 359-363, 1998). More particularly, neurodegeneration underlies several progressive CNS disorders, including, but not limited to, Alzheimer's disease, Parkinson's disease, amyotrophic lateral sclerosis, Huntington's disease, dementia with Lewy bodies, as well as diminished CNS function resulting from traumatic brain injury. For example, the impaired function of α7 NNRs by β-amyloid peptides linked to Alzheimer's disease has been implicated as a key factor in development of the cognitive deficits associated with the disease (Liu, Q.-S., Kawai, H., Berg, D. K., Proc. Natl. Acad. Sci. USA 98: 4734-4739, 2001). α7 selective ligands can influence neuroprotective pathways leading to decreased phosphorylation of the tau protein, whose hyperphosphorylation is required for neurofibrillary tangle formation in various tau related pathologies such as Alzheimer's disease and various other dementias (Bitner et al., Soc. Neuroscience, 2006 abst 325.6). The activation of α7 NNRs has been shown to block this neurotoxicity (Kihara, T. et al., J. Biol. Chem. 276: 13541-13546, 2001). As such, selective ligands that enhance α7 activity can counter the deficits of Alzheimer's and other neurodegenerative diseases.

α7 NNRs also have been implicated in aspects of neurodevelopment, for example neurogenesis of the brain (Falk, L. et al., Developmental Brain Research 142:151-160, 2003; Tsuneki, H., et al., J. Physiol. (London) 547:169-179, 2003; Adams, C. E., et al., Developmental Brain Research 139:175-187, 2002). As such, α7 NNRs can be useful in preventing or treating conditions or disorders associated with impaired neurodevelopment, for example schizophrenia. (Sawa A., Mol. Med. 9:3-9, 2003).

Several compounds with high affinity for α4β2 NNRs have been shown to improve attentive and cognitive performance in preclinical models that are relevant to attention-deficit/hyperactivity disorder (ADHD), a disease characterized by core symptoms of hyperactivity, inattentiveness, and impulsivity. For example, ABT-418, a full agonist at α4β2 NNRs, is efficacious in a variety of preclinical cognition models. ABT-418 administered transdermally, was shown in a controlled clinical trial in 32 adults to be effective in treating ADHD in general, and attentional/cognitive deficits in particular (Wilens, T. E.; Biederman, J.; Spencer, T. J.; Bostic, J.; Prince, J.; Monuteaux, M. C.; Soriano, J.; Fince, C.; Abrams, A.; Rater, M.; Polisner, D. The American Journal of Psychiatry (1999)156(12), 1931-1937.). Likewise, ABT-418 showed a signal of efficacy in a pilot Alzheimer's disease trial. ABT-089, a α4β2 selective partial agonist, has been shown in rodent and primate animal models to improve attention, learning, and memory deficits. ABT-089 and another α4β2 agonist, ispronicline have shown efficacy in a pilot clinical trials (Wilens, T. E.; Verlinden, M. H.; Adler, L. A.; Wozniak, P. J.; West, S. A. Biological Psychiatry (2006), 59(11), 1065-1070. Geerts, H. Curr. Opin. Invest. Drugs (2006), 7(1), 60-69). In addition to cognition, compounds that interact with α4β2 NNRs such as ABT-594 and others are also efficacious in preclinical and clinical models of pain. As such, ligands that modulate both α7 and α4β2 activity can have broader spectrum of therapeutic efficacy in disease states such as those involving cognitive and attentive deficits, pain, neurodegenerative diseases and others.

Schizophrenia is a complex disease that is characterized by abnormalities in perception, cognition, and emotions. Significant evidence implicates the involvement of α7 NNRs in this disease, including a measured deficit of these receptors in post-mortem patients (Sawa A., Mol. Med. 9:3-9, 2003; Leonard, S. Eur. J. Pharmacol. 393: 237-242, 2000). Deficits in sensory processing (gating) are one of the hallmarks of schizophrenia. These deficits can be normalized by nicotinic ligands that operate at the α7 NNR (Adler L. E. et al., Schizophrenia Bull. 24: 189-202, 1998; Stevens, K. E. et al., Psychopharmacology 136: 320-327, 1998). More recent studies have shown that α4β2 nicotinic receptor stimulation also contributes to the effects of nicotine in the DBA/2 mouse model of sensory gating (Radek et al., Psychopharmacology (Berl). 2006 187:47-55). Thus, α7 and α7/α4β2 ligands demonstrate potential in the treatment schizophrenia.

A population of α7 or α4β2 NNRs in the spinal cord modulate neurotransmission that has been associated with the pain-relieving effects of nicotinic compounds (Cordero-Erausquin, M. and Changeux, J.-P. Proc. Natl. Acad. Sci. USA 98:2803-2807, 2001). The α7 NNR or and α7/α4β2 ligands demonstrate therapeutic potential for the treatment of pain states, including acute pain, post-surgical pain, as well as chronic pain states including inflammatory pain and neuropathic pain.

Compounds of the invention are particularly useful for treating and preventing a condition or disorder affecting memory, cognition, neurodegeneration, neurodevelopment, and schizophrenia.

Cognitive impairment associated with schizophrenia (CDS) often limits the ability of patients to function normally, a symptom not adequately treated by commonly available treatments, for example, treatment with an atypical antipsychotic. (Rowley, M. et al., J. Med. Chem. 44: 477-501, 2001). Such cognitive deficit has been linked to dysfunction of the nicotinic cholinergic system, in particular with decreased activity at α7 receptors. (Friedman, J. I. et al., Biol. Psychiatry, 51: 349-357, 2002). Thus, activators of α7 receptors can provide useful treatment for enhancing cognitive function in schizophrenic patients who are being treated with atypical antipsychotics. Accordingly, the combination of an α7 nAChR ligand and one or more atypical antipsychotic would offer improved therapeutic utility. Specific examples of suitable atypical antipsychotics include, but are not limited to, clozapine, risperidone, olanzapine, quietapine, ziprasidone, zotepine, iloperidone, and the like.

Compounds of the invention may be administered alone or in combination (i.e. co-administered) with one or more additional pharmaceutical agents. Combination therapy includes administration of a single pharmaceutical dosage formulation containing one or more of the compounds of invention and one or more additional pharmaceutical agents, as well as administration of the compounds of the invention and each additional pharmaceutical agent, in its own separate pharmaceutical dosage formulation. For example, a compound of formula (I) and one or more additional pharmaceutical agents, may be administered to the patient together, in a single oral dosage composition having a fixed ratio of each active ingredient, such as a tablet or capsule; or each agent may be administered in separate oral dosage formulations.

Where separate dosage formulations are used, compounds of the invention and one or more additional pharmaceutical agents may be administered at essentially the same time (e.g., concurrently) or at separately staggered times (e.g., sequentially).

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salts thereof. Compounds of the invention can also be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal range from about 0.10 μg/kg body weight to about 10 mg/kg body weight. More preferable doses can be in the range of from about 0.10 μg/kg body weight to about 1 mg/kg body weight. If desired, the effective daily dose can be divided into multiple doses for purposes of administration. Consequently, single dose compositions may contain such amounts or submultiples thereof to make up the daily dose.

Methods for Preparing Compounds of the Invention

This invention is intended to encompass compounds of the invention when prepared by synthetic processes or by metabolic processes. Preparation of the compounds of the invention by metabolic processes include those occurring in the human or animal body (in vivo) or processes occurring in vitro.

The synthesis of compounds of formula (I) wherein the groups $Y^2$ and A have the meanings as set forth in the summary section unless otherwise noted, is exemplified in Schemes 1-3.

As used in the descriptions of the schemes and the examples, certain abbreviations are intended to have the following meanings: MeOH for methanol, HPLC for high pressure liquid chromatography, and Tris for tris(hydroxymethyl) aminomethane.

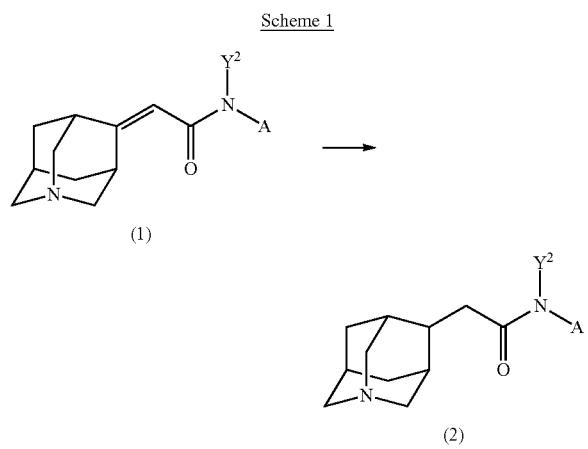

As shown in Scheme 1, hydrogenation of compounds of formula (I) in the presence of a catalyst provides compounds of formula (2). Examples of suitable catalysts include, but are not limited to, palladium on carbon, and Raney nickel. The reaction is usually conducted in a solvent such as but not limited to methanol and at ambient or elevated temperatures.

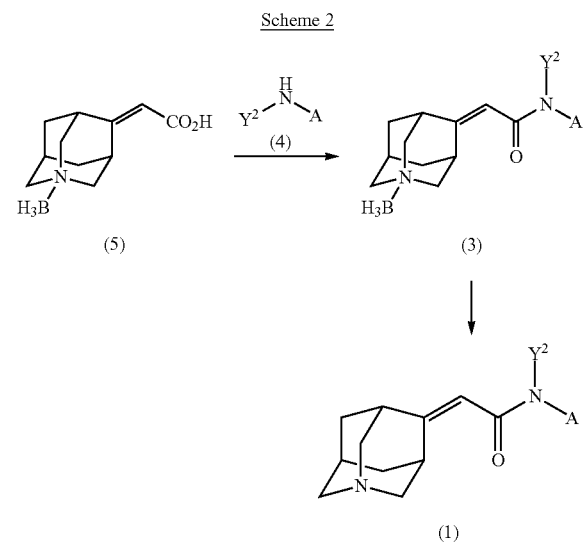

2-(1-Azaadamantan-4-ylidene)acetic acid borane complex of formula (5), prepared as described in Example 1C, when treated with an amine of formula (4) or salts thereof, utilizing conditions known to those skilled in the art for generating amides from carboxylic acids, will provide compounds of formula (3). For example, the reaction can be conducted in the presence of a coupling reagent such as but not limited to 1-(3-dimethylaminopropyl)-3-ethylcarbodiimide hydrochloride (EDCI), 1,3-dicyclohexylcarbodiimide (DCC), bis(2-oxo-3-oxazolidinyl)phosphinic chloride (BOPCl), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU). The coupling reagents may be added as a solid, a solution or as the reagent bound to a solid support resin. In addition to the coupling reagents, presence of auxiliary-coupling reagents may facilitate the coupling reaction. Auxiliary coupling reagents that are often used in the coupling reactions include but are not limited to 4-dimethylaminopyridine, 1-hydroxy-7-azabenzotriazole (HOAT) and 1-hydroxybenzotriazole hydrate (HOBT). The reaction is optionally performed in the presence of a base (for example, an organic base such as N-methylmorpholine, pyridine, diisopropylethylamine, and the like). The coupling reaction can be carried out in solvents such as, but not limited to, tetrahydrofuran, N,N,-dimethylformamide, dichloromethane, and ethyl acetate. The reaction may be conducted at ambient or elevated temperatures.

Compounds of formula (3) when treated with aqueous hydrochloric acid in a solvent such as but not limited to acetone and at ambient temperature will provide compounds of formula (1).

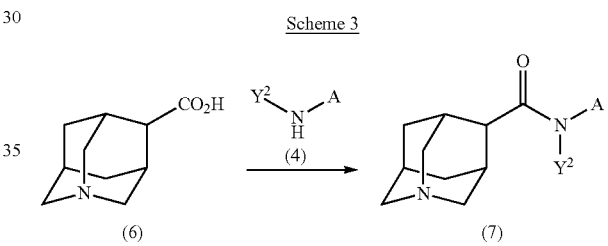

Individual stereoisomers of 1-azatricyclo[3.3.1.1$^{3,7}$]decane-4-carboxylic acid (6) can be prepared from azaadamantan-4-one as shown in the Examples 21A and 21B. Derivatization of each of the stereoisomeric carboxylic acids, or mixtures thereof, to the corresponding amides of formula (7) can be achieved utilizing the amide bond forming reaction conditions as described in Scheme 2.

It will be appreciated that the synthetic schemes and specific examples as illustrated in the synthetic examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Synthetic Examples section. Reactions may be worked up in the convention manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

The compounds of the invention and processes for making compounds for the method of the invention will be better understood by reference to the following examples, which are intended as an illustration of and not a limitation upon the scope of the invention.

EXAMPLES

Example 1

2-[1-azatricyclo[3.3.1.1$^{3,7}$]dec-4-ylidene]-N-(4-methylphenyl)acetamide

Example 1A 1-azatricyclo[3.3.1.1$^{3,7}$]decan-4-one borane complex 1-azatricyclo[3.3.1.1$^{3,7}$]decan-4-one (prepared as described in Becker, D. P., Flynn, D. L. *Synthesis* 1992, 1080-1082) (1.54 g, 10.2 mmol) was dissolved in acetone (10 mL) and the mixture was chilled to −78° C. To the reaction mixture was added a solution of borane-tetrahydrofuran complex (1 M in tetrahydrofuran, 11 mL, 11 mmol). The reaction was stirred at −78° C. for 1 hour. The reaction was then diluted with water (50 mL) and extracted with CHCl$_3$ (3×50 mL). The organic extracts were combined and washed with brine (50 mL), dried over Na$_2$SO$_4$, filtered and concentrated. The residue was purified by silica gel chromatography (5% ethyl acetate in CH$_2$Cl$_2$, R$_f$=0.44) to afford the title compound as a white solid. $^1$H NMR (CDCl$_3$, 300 MHz) δ 1.13-1.85 (br m, 3H; BH$_3$), 2.08-2.23 (m, 5H), 2.61 (s, 2H), 3.32-3.44 (m, 6H) ppm. MS (DCI/NH$_3$) m/z 181 (M+NH$_3$—H)$^+$.

Example 1B

Methyl 2-(1-azaadamantan-4-ylidene)acetate borane complex

Sodium hydride (0.64 g, 60 wt %, 16.0 mmol) was suspended in tetrahydrofuran (20 mL) and the mixture was chilled to 0° C. Methyl diethylphosphonoacetate (2.2 mL, 12.1 mmol) was added, and the reaction mixture stirred at 0° C. for 1 hour. The reaction was then chilled to −78° C., and Example 1A (1.34 g, 8.12 mmol) was added and rinsed in with tetrahydrofuran (2×10 mL). The reaction was allowed to slowly warm to ambient temperature and was stirred at ambient temperature overnight (16 hours). The reaction was then diluted with water (200 mL), and extracted with CH$_2$Cl$_2$ (3×100 mL). The organic extracts were combined and washed with brine (100 mL), dried over MgSO$_4$, filtered and concentrated. The residue was purified by silica gel chromatography (2.5% ethyl acetate in CH$_2$Cl$_2$) to afford the title compound. $^1$H NMR (CDCl$_3$, 300 MHz) δ 1.05-1.80 (br m, 3H; BH$_3$), 1.89-2.13 (m, 5H), 2.52 (s, 1H), 3.17-3.26 (m, 6H), 3.71 (s, 3H), 4.20 (s, 1H), 5.73 (s, 1H) ppm. MS (DCI/NH$_3$) m/z 237 (M+NH$_3$—H)$^+$.

Example 1C 2-(1-Azaadamantan-4-ylidene)acetic acid borane complex

Example 1B (1.36 g, 6.15 mmol) was dissolved in ethanol (40 mL). 2 M NaOH (aqueous) (16 mL) was added, and the reaction stirred at ambient temperature for 3 hours. The reaction was acidified to pH 2 with 2 M HCl (aqueous). The reaction was then diluted with water (100 mL), and extracted with CH$_2$Cl$_2$ (3×100 mL). The organic extracts were combined and washed with brine (100 mL), dried over Na$_2$SO$_4$, filtered and concentrated to afford the title compound. $^1$H NMR (CDCl$_3$, 300 MHz) δ 1.89-2.14 (m, 5H), 2.56 (s, 1H), 3.13-3.27 (m, 6H), 4.17 (s, 1H), 5.76 (s, 1H) ppm. MS (DCI/NH$_3$) m/z 223 (M+NH$_3$—H)$^+$.

Example 1D

N-(p-Tolyl)-2-(1-azaadamantan-4-ylidene)acetamide borane complex

Example 1C (104.6 mg, 0.51 mmol) was dissolved in CH$_2$Cl$_2$ (5 mL). p-Toluidine (141.2 mg, 1.32 mmol), N-hydroxybenzotriazole (81.0 mg, 0.60 mmol), 4-dimethylaminopyridine (16.9 mg, 0.14 mmol) and ethyl-3(3-dimethyl amino) propyl carbodiimide-HCl Salt (131.2 mg, 0.68 mmol) were added to the reaction mixture. The reaction was stirred at ambient temperature for 17 hours and was then concentrated. The residue was purified by preparative HPLC on a Waters Nova-Pak® HR C18 6 um 60 Å Prep-Pak® cartridge column (40 mm×100 mm) using a gradient of 10% to 100% acetonitrile in 10 mM aqueous ammonium acetate over 12 minutes at a flow rate of 70 mL/minute to provide the title compound. $^1$H NMR (CDCl$_3$, 300 MHz) δ 1.93-2.13 (m, 5H), 2.32 (s, 3H), 2.49 (s, 1H), 3.20-3.25 (m, 6H), 4.42 (s, 1H), 5.74 (s, 1H), 7.12-7.14 (m, 3H), 7.40 (d, J=8.14 Hz, 2H) ppm. MS (DCI/NH$_3$) m/z 297.1 (M+H)$^+$.

Example 1E

2-[1-azatricyclo[3.3.1.1$^{3,7}$]dec-4-ylidene]-N-(4-methylphenyl)acetamide

Example 1D (148.6 mg, 0.31 mmol) was dissolved in acetone (4.5 mL). 3 M HCl (aqueous) (1.5 mL) was added to the reaction mixture and it was stirred at ambient temperature for 3 hours. The reaction was concentrated, dissolved in methanol and stirred for 1 hour. The reaction was concentrated again and the product triturated from diethyl ether/methanol 9:1 (10 mL) to afford the title compound as the hydrochloride salt. $^1$H NMR (methanol-d$_4$, 300 MHz) δ 2.06-2.10 (m, 2H), 2.25-2.35 (m, 6H), 2.79 (s, 1H), 3.53-3.60 (m, 2H), 3.68-3.76 (m, 4H), 4.56 (s, 1H), 6.05 (s, 1H), 7.12 (d, J=8.5 Hz, 2H), 7.43-7.46 (m, 2H) ppm; MS (DCI/NH$_3$) m/z 283 (M+H)$^+$; Anal. (C$_{18}$H$_{22}$N$_2$O.HCl.0.15H$_2$O)C, H, N, Cl.

Example 2

2-[1-azatricyclo[3.3.1.1$^{3,7}$]dec-4-ylidene]-N-phenylacetamide

Example 2A

N-phenyl-2-(1-azaadamantan-4-ylidene)acetamide borane complex

The title compound was prepared as described in Example 1D, substituting aniline for p-toluidine. MS (DCI/NH$_3$) m/z 283 (M+H)$^+$.

Example 2B

2-[1-azatricyclo[3.3.1.1$^{3,7}$]dec-4-ylidene]-N-phenylacetamide

The hydrochloride salt of the title compound was prepared as described in Example 1E, substituting Example 2A for Example 1D. $^1$H NMR (methanol-d$_4$, 300 MHz) δ 2.07-2.11 (m, 2H), 2.26-2.36 (m, 3H), 2.80 (s, 1H), 3.54-3.60 (m, 2H), 3.68-3.76 (m, 4H), 4.57 (s, 1H), 6.06 (s, 1H), 7.07-7.12 (m, 1H), 7.28-7.33 (m, 2H), 7.56-7.59 (m, 2H) ppm; MS (DCI/NH$_3$) m/z 269 (M+H)$^+$; Anal. (C$_{17}$H$_{20}$N$_2$.1.05HCl.0.15H$_2$O) C, H, N, Cl.

Example 3

2-[1-azatricyclo[3.3.1.1$^{3,7}$]dec-4-ylidene]-N-1-naphthylacetamide

Example 3A

N-(1-naphthyl)-2-(1-azaadamantan-4-ylidene)acetamide borane complex

The title compound was prepared as described in Example 1D, substituting 1-napthylamine for p-toluidine. MS (DCI/NH$_3$) m/z 333 (M+H)$^+$.

Example 3B

2-[1-azatricyclo[3.3.1.1$^{3,7}$]dec-4-ylidene]-N-1-naphthylacetamide

The hydrochloride salt of the title compound was prepared as described in Example 1E, substituting Example 3A for Example 1D. $^1$H NMR (methanol-d$_4$, 300 MHz) δ 2.09-2.18 (m, 2H), 2.26-2.38 (m, 3H), 2.87 (s, 1H), 3.58-3.79 (m, 6H), 4.59 (s, 1H), 6.30 (s, 1H), 7.47-7.56 (m, 3H), 7.63-7.65 (m, 1H), 7.79 (d, J=8.1 Hz, 1H), 7.88-7.92 (m, 1H), 7.96-7.99 (m, 1H) ppm; MS (DCI/NH$_3$) m/z 319 (M+H)$^+$; Anal. (C$_{21}$H$_{22}$N$_2$O.1.25 HCl.0.2H$_2$O)C, H, N, Cl.

Example 4

2-[1-azatricyclo[3.3.1.1$^{3,7}$]dec-4-ylidene]-N-(3-chlorophenyl)acetamide

Example 4A

N-(3-chlorophenyl)-2-(1-azaadamantan-4-ylidene) acetamide borane complex

The title compound was prepared as described in Example 1D, substituting 3-chloroaniline for p-toluidine. MS (DCI/NH$_3$) m/z 232 (M+NH$_3$—H)$^+$.

Example 4B

2-[1-azatricyclo[3.3.1.1$^{3,7}$]dec-4-ylidene]-N-(3-chlorophenyl)acetamide

The hydrochloride salt of the title compound was prepared as described in Example 1E, substituting Example 4A for Example 1D. $^1$H NMR (methanol-d$_4$, 300 MHz) δ 2.07-2.12 (m, 2H), 2.27-2.35 (m, 3H), 2.79 (s, 1H), 3.54-3.60 (m, 2H), 3.68-3.76 (m, 4H), 4.57 (s, 1H), 6.04 (s, 1H), 7.08-7.11 (m, 1H), 7.28 (t, J=7.97 Hz, 1H), 7.41-7.44 (m, 1H), 7.80 (t, J=2.03 Hz, 1H) ppm; MS (DCI/NH$_3$) m/z 303 (M+H)$^+$; Anal. (C$_{17}$H$_{19}$ClN$_2$O.1.15HCl) C, H, N.

Example 5

2-[1-azatricyclo[3.3.1.1$^{3,7}$]dec-4-ylidene]-N-(4-tert-butylphenyl)acetamide

Example 5A

N-(4-tert-butylphenyl)-2-(1-azaadamantan-4-ylidene)acetamide borane complex

The title compound was prepared as described in Example 1D, substituting 4-tert-butylaniline for p-toluidine. MS (DCI/NH$_3$) m/z 339 (M+H)$^+$.

Example 5B

2-[1-azatricyclo[3.3.1.1$^{3,7}$]dec-4-ylidene]-N-(4-tert-butylphenyl)acetamide

The hydrochloride salt of the title compound was prepared as described in Example 1E, substituting Example 5A for Example 1D. $^1$H NMR (methanol-d$_4$, 300 MHz) δ 1.31 (s, 9H), 2.06-2.11 (m, 2H), 2.26-2.35 (m, 3H), 2.79 (s, 1H), 3.53-3.60 (m, 2H), 3.68-3.76 (m, 4H), 4.57 (s, 1H), 6.05 (s, 1H), 7.33-7.38 (m, 2H), 7.46-7.51 (m, 2H) (m, 2H) ppm; MS (DCI/NH$_3$) m/z 325 (M+H)$^+$; Anal. (C$_{21}$H$_{28}$N$_2$O.1.3HCl.H$_2$O)C, H, N, Cl.

Example 6

2-[1-azatricyclo[3.3.1.1$^{3,7}$]dec-4-ylidene]-N-[4-(trifluoromethoxy)phenyl]acetamide

Example 6A

N-(4-trifluoromethoxyphenyl)-2-(1-azaadamantan-4-ylidene)acetamide borane complex The title compound was prepared as described in Example 1D, substituting 4-trifluoromethoxyaniline for p-toluidine. MS (DCI/NH$_3$) m/z 382 (M+NH$_3$—H)$^+$.

Example 6B

2-[1-azatricyclo[3.3.1.1$^{3,7}$]dec-4-ylidene]-N-[4-(trifluoromethoxy)phenyl]acetamide The hydrochloride salt of the title compound was prepared as described in Example 1E, substituting Example 6A for Example 1D. $^1$H NMR (methanol-d$_4$, 300 MHz) δ 1.31 (s, 9H), 2.06-2.12 (m, 2H), 2.27-2.36 (m, 3H), 2.80 (s, 1H), 3.54-3.61 (m, 2H), 3.68-3.76 (m, 4H), 4.58 (s, 1H), 6.05 (s, 1H), 7.21-7.24 (m, 2H), 7.66-7.71 (m, 2H) ppm; MS (DCI/NH$_3$) m/z 353 (M+H)$^+$; Anal. (C$_{21}$H$_{28}$N$_2$O.1.1HCl) C, H, N, Cl.

Example 7

2-[1-azatricyclo[3.3.1.1$^{3,7}$]dec-4-ylidene]-N-[4-(trifluoromethyl)phenyl]acetamide

Example 7A

N-(4-trifluoromethylphenyl)-2-(1-azaadamantan-4-ylidene)acetamide borane complex The title compound was prepared as described in Example 1D, substituting 4-trifluoromethylaniline for p-toluidine. MS (DCI/NH$_3$) m/z 366 (M+NH$_3$—H)$^+$.

Example 7B

2-[1-azatricyclo[3.3.1.1$^{3,7}$]dec-4-ylidene]-N-[4-(trifluoromethyl)phenyl]acetamide The hydrochloride salt of the title compound was prepared as described in Example 1E, substituting Example 7A for Example 1D. $^1$H NMR (methanol-d$_4$, 300 MHz) δ 2.07-2.12 (m, 2H), 2.27-2.37 (m, 3H), 2.81 (s, 1H), 3.54-3.61 (m, 2H), 3.69-3.77 (m, 4H), 4.58 (s, 1H), 6.08 (s, 1H), 7.60 (d, J=8.8 Hz, 2H), 7.80 (d, J=8.5 Hz, 2H) ppm; MS (DCI/NH$_3$) m/z 337 (M+H)$^+$; Anal. (C$_{18}$H$_{19}$F$_3$N$_2$O.HCl) C, H, N, Cl.

Example 8

2-[1-azatricyclo[3.3.1.1$^{3,7}$]dec-4-ylidene]-N-(4-chloro-1-naphthyl)acetamide

Example 8A

N-(1-4-chloronaphth-1-yl)-2-(1-azaadamantan-4-ylidene)acetamide borane complex

The title compound was prepared as described in Example 1D, substituting 1-amino-4-chloronaphthalene for p-toluidine. MS (DCI/NH$_3$) m/z 353 (M+NH$_3$—H)$^+$.

Example 8B

2-[1-azatricyclo[3.3.1.1$^{3,7}$]dec-4-ylidene]-N-(4-chloro-1-naphthyl)acetamide The hydrochloride salt of the title compound was prepared as described in Example 1E, substituting Example 8A for Example 1D. $^1$H NMR (methanol-d$_4$, 300 MHz) δ 2.09-2.18 (m, 2H), 2.26-2.39 (m, 3H), 2.87 (s, 1H), 3.58-3.79 (m, 6H), 4.58 (s, 1H), 6.29 (s, 1H), 7.62-7.71 (m, 4H), 8.03-8.06 (m, 1H), 8.28-8.31 (m, 1H), ppm; MS (DCI/NH$_3$) m/z 353 (M+H)$^+$; Anal. (C$_{21}$H$_{22}$N$_2$O.HCl.1.3H$_2$O)C, H, N, Cl.

Example 9

2-[1-azatricyclo[3.3.1.1$^{3,7}$]dec-4-ylidene]-N-(4-bromophenyl)acetamide

Example 9A

N-(4-bromophenyl)-2-(1-azaadamantan-4-ylidene)acetamide borane complex

The title compound was prepared as described in Example 1D, substituting 4-bromoaniline for p-toluidine. MS (DCI/NH$_3$) m/z 347 (M-BH$_3$+H)$^+$.

Example 9B

2-[1-azatricyclo[3.3.1.1$^{3,7}$]dec-4-ylidene]-N-(4-bromophenyl)acetamide

The hydrochloride salt of the title compound was prepared as described in Example 1E, substituting Example 9A for Example 1D. $^1$H NMR (methanol-d$_4$, 300 MHz) δ 2.07-2.11 (m, 2H), 2.26-2.35 (m, 3H), 2.79 (s, 1H), 3.53-3.60 (m, 2H), 3.68-3.76 (m, 4H), 4.57 (s, 1H), 6.04 (s, 1H), 7.42-4.47 (m, 2H), 7.52-7.56 (m, 2H) ppm; MS (DCI/NH$_3$) m/z 347 (M+H)$^+$; Anal. (C$_{17}$H$_{19}$BrN$_2$O.1.2HCl) C, H, N.

Example 10

2-[1-azatricyclo[3.3.1.1$^{3,7}$]dec-4-ylidene]-N-pyridin-3-ylacetamide

Example 10A

N-(3-pyridinyl)-2-(1-azaadamantan-4-ylidene)acetamide borane complex

The title compound was prepared as described in Example 1D, substituting 3-aminopyridine for p-toluidine. MS (DCI/NH$_3$) m/z 270 (M-BH$_3$+H)$^+$.

Example 10B

2-[1-azatricyclo[3.3.1.1$^{3,7}$]dec-4-ylidene]-N-pyridin-3-ylacetamide

The hydrochloride salt of the title compound was prepared as described in Example 1E, substituting Example 10A for Example 1D. $^1$H NMR (methanol-d$_4$, 300 MHz) δ 2.03-2.11 (m, 2H), 2.30-2.39 (m, 3H), 2.80 (s, 1H), 3.54-3.63 (m, 2H), 3.70-3.79 (m, 4H), 4.60 (s, 1H), 6.13 (s, 1H), 8.03 (dd, J=8.65, 5.59 Hz, 1H), 8.51-8.56 (m, 2H), 9.49 (d, J=2.03 Hz, 1H) ppm; MS (DCI/NH$_3$) m/z 270 (M+H)$^+$; Anal. (C$_{16}$H$_{19}$N$_3$O.2 HCl.0.65H$_2$O)C, H, N.

Example 11

2-[-1-azatricyclo[3.3.1.1$^{3,7}$]dec-4-ylidene]-N-pyridin-2-ylacetamide

Example 11A

N-(2-pyridinyl)-2-(1-azaadamantan-4-ylidene)acetamide borane complex

The title compound was prepared as described in Example 1D, substituting 1-aminopyridine for p-toluidine, except it was stirred at 40° C. for 18 hours. MS (DCI/NH$_3$) m/z 284 (M+H)$^+$.

Example 11B

2-[-1-azatricyclo[3.3.1.1³,⁷]dec-4-ylidene]-N-pyridin-2-ylacetamide

The hydrochloride salt of the title compound was prepared as described in Example 1E, substituting Example 11A for Example 1D. ¹H NMR (methanol-$d_4$, 300 MHz) δ 2.09-2.14 (m, 2H), 2.34-2.42 (m, 3H), 2.92 (s, 1H), 3.58-3.65 (m, 2H), 3.72-3.81 (m, 4H), 4.58 (s, 1H), 6.19 (s, 1H), 7.55-7.64 (m, 2H), 8.39-8.48 (m, 2H) ppm; MS (DCI/NH$_3$) m/z 270 (M+H)$^+$; Anal. ($C_{16}H_{19}N_3O.2HCl.1.55H_2O$)C, H, N.

Example 12

2-[1-azatricyclo[3.3.1.1³,⁷]dec-4-ylidene]-N-quinolin-6-ylacetamide

Example 12A

N-(6-quinolinyl)-2-(1-azaadamantan-4-ylidene)acetamide borane complex

The title compound was prepared as described in Example 1D, substituting 6-aminoquinoline for p-toluidine. MS (DCI/NH$_3$) m/z 334 (M+H)$^+$.

Example 12B

2-[1-azatricyclo[3.3.1.1³,⁷]dec-4-ylidene]-N-quinolin-6-ylacetamide

The hydrochloride salt of the title compound was prepared as described in Example 1E, substituting Example 12A for Example 1D. ¹H NMR (methanol-$d_4$, 300 MHz) δ 2.08-2.13 (m, 2H), 2.31-2.40 (m, 3H), 2.86 (s, 1H), 3.57-3.64 (m, 2H), 3.71-3.80 (m, 4H), 4.65 (s, 1H), 6.18 (s, 1H), 8.05 (dd, J=8.31, 5.59 Hz, 1H), 8.20-8.29 (m, 2H), 8.86 (s, 1H), 9.06-9.12 (m, 2H) ppm; MS (DCI/NH$_3$) m/z 320 (M+H)$^+$; Anal. ($C_{16}H_{19}N_3O.2HCl.0.6H_2O$)C, H, N, Cl.

Example 13

2-[1-azatricyclo[3.3.1.1³,⁷]dec-4-ylidene]-N-(4-chlorophenyl)acetamide

Example 13A

N-(4-chlorophenyl)-2-(1-azaadamantan-4-ylidene)acetamide borane complex

The title compound was prepared as described in Example 1D, substituting 4-chloroaniline for p-toluidine. MS (DCI/NH$_3$) m/z 332 (M+NH$_3$—H)$^+$.

Example 13B

2-[1-azatricyclo[3.3.1.1³,⁷]dec-4-ylidene]-N-(4-chlorophenyl)acetamide

Example 13A (98.7 mg, 0.31 mmol) was dissolved in acetone (3 mL). 3 M HCl (aqueous) (1.5 mL) was added to the reaction mixture and it stirred at ambient temperature for 2 hours. The reaction was diluted with 1 M NaOH (aqueous) (35 mL) and extracted with CH$_2$Cl$_2$ (3×35 mL). The organic extracts were combined and dried over Na$_2$SO$_4$, filtered and concentrated. The residue was dissolved in diethyl ether/methanol 9:1 (10 mL) and salted out with fumaric acid to afford the title compound as a fumarate salt. ¹H NMR (methanol-$d_4$, 300 MHz) δ 2.06-2.10 (m, 2H), 2.25-2.35 (m, 3H), 2.75 (s, 1H), 3.49-3.56 (m, 2H), 3.64-3.72 (m, 4H), 4.53 (s, 1H), 6.02 (s, 1H), 6.69 (s, 2H; $C_4H_4O_4$), 7.28-7.32 (m, 2H), 7.56-7.61 (m, 2H) ppm; MS (DCI/NH$_3$) m/z 303 (M+H)$^+$; Anal. ($C_{17}H_{19}ClN_2O.C_4H_4O_4.0.55H_2O$)C, H, N.

Example 14

2-[1-azatricyclo[3.3.1.1³,⁷]dec-4-ylidene]-N-2-naphthylacetamide

Example 14A

N-(2-naphthalyl)-2-(1-azaadamantan-4-ylidene)acetamide borane complex

The title compound was prepared as described in Example 1D, substituting 2-naphthylamine for p-toluidine. MS (DCI/NH$_3$) m/z 333 (M+H)$^+$.

Example 14B

2-[1-azatricyclo[3.3.1.1³,⁷]dec-4-ylidene]-N-2-naphthylacetamide

The fumarate salt of the title compound was prepared as described in Example 13B, substituting Example 14A for Example 13A. ¹H NMR (methanol-$d_4$, 300 MHz) δ 2.09-2.13 (m, 2H), 2.28-2.35 (m, 3H), 2.79 (s, 1H), 3.52-3.59 (m, 2H), 3.65-3.74 (m, 4H), 4.59 (s, 1H), 6.11 (s, 1H), 6.69 (s, 2H; $C_4H_4O_4$), 7.39-7.48 (m, 2H), 7.56 (dd, J=8.82, 2.03 Hz, 1H), 7.75-7.83 (m, 3H), 8.25 (d, J=2.03 Hz, 1H) ppm; MS (DCI/NH$_3$) m/z 319 (M+H)$^+$; Anal. ($C_{21}H_{22}N_2O.1.1C_4H_4O_4$) C, H, N.

Example 15

2-[1-azatricyclo[3.3.1.1³,⁷]dec-4-ylidene]-N-(4-chlorobenzyl)acetamide

Example 15A

N-(4-chlorobenzyl)-2-(1-azaadamantan-4-ylidene)acetamide borane complex

The title compound was prepared as described in Example 1D, substituting 4-chlorobenzylamine for p-toluidine. MS (DCI/NH$_3$) m/z 346 (M+NH$_3$—H)$^+$.

Example 15B

2-[1-azatricyclo[3.3.1.1³,⁷]dec-4-ylidene]-N-(4-chlorobenzyl)acetamide

The fumarate salt of the title compound was prepared as described in Example 13B, substituting Example 15A for Example 13A. ¹H NMR (methanol-$d_4$, 300 MHz) δ 2.02-2.05 (m, 2H), 2.15-2.30 (m, 3H), 2.61 (s, 1H), 3.36-3.43 (m, 2H), 3.53-3.61 (m, 4H), 4.33 (s, 1H), 4.37 (s, 2H), 5.86 (s, 1H), 6.67 (s, 2H; C₄H₄O₄), 7.25-7.33 (m, 4H) ppm; MS (DCI/NH₃) m/z 317 (M+H)⁺; Anal. (C$_{18}$H$_{21}$ClN$_2$O.C$_4$H$_4$O$_4$) C, H, N.

Example 16

2-[1-azatricyclo[3.3.1.1$^{3,7}$]dec-4-ylidene]-N-1,1'-biphenyl-4-ylacetamide

Example 16A

N-(4-biphenyl)-2-(1-azaadamantan-4-ylidene)acetamide borane complex

The title compound was prepared as described in Example 1D, substituting 4-aminobiphenyl for p-toluidine. MS (DCI/NH₃) m/z 345 (M-BH₃+H)⁺.

Example 16B

2-[1-azatricyclo[3.3.1.1$^{3,7}$]dec-4-ylidene]-N-1,1'-biphenyl-4-ylacetamide

The fumarate salt of the title compound was prepared as described in Example 13B, substituting Example 16A for Example 13A. ¹H NMR (methanol-d₄, 300 MHz) δ 2.07-2.12 (m, 2H), 2.20-2.35 (m, 3H), 2.69 (s, 1H), 3.47-3.67 (m, 6H), 4.48 (s, 1H), 6.03 (s, 1H), 6.68 (s, 2H; C₄H₄O₄), 7.27-7.33 (m, 1H), 7.38-7.44 (m, 2H), 7.57-7.61 (m, 4H), 7.65-7.69 (m, 2H) ppm; MS (DCI/NH₃) m/z 345 (M+H)⁺; Anal. (C$_{23}$H$_{24}$N$_2$O.C$_4$H$_4$O$_4$)C, H, N.

Example 17

2-[1-azatricyclo[3.3.1.1$^{3,7}$]dec-4-ylidene]-N-(4-fluorophenyl)acetamide

Example 17A

N-(4-biphenyl)-2-(1-azaadamantan-4-ylidene)acetamide borane complex

The title compound was prepared as described in Example 1D, substituting 4-fluoroaniline for p-toluidine. MS (DCI/NH₃) m/z 316 (M+NH₃—H)⁺.

Example 17B

2-[1-azatricyclo[3.3.1.1$^{3,7}$]dec-4-ylidene]-N-(4-fluorophenyl)acetamide

The fumarate salt of the title compound was prepared as described in Example 13B, substituting Example 17A for Example 13A. ¹H NMR (methanol-d₄, 300 MHz) δ 2.05-2.12 (m, 2H), 2.25-2.34 (m, 3H), 2.76 (s, 1H), 3.50-3.56 (m, 2H), 3.64-3.72 (m, 4H), 4.53 (s, 1H), 6.02 (s, 1H), 6.68 (s, 2.6H; C₄H₄O₄), 7.01-7.06 (m, 2H), 7.54-7.61 (m, 2H) ppm; MS (DCI/NH₃) m/z 287 (M+H)⁺; Anal. (C$_{17}$H$_{19}$FN$_2$O.1.4; C$_4$H$_4$O$_4$) C, H, N.

Example 18

2-[1-azatricyclo[3.3.1.1$^{3,7}$]dec-4-ylidene]-N-1,3-benzodioxol-5-ylacetamide

Example 18A

N-(3,4-methylenedioxyphenyl)-2-(1-azaadamantan-4-ylidene)acetamide borane complex The title compound was prepared as described in Example 1D, substituting 3,4-(methylenedioxy)aniline for p-toluidine. MS (DCI/NH₃) m/z 313 (M-BH₃+H)⁺.

Example 18B

2-[1-azatricyclo[3.3.1.1$^{3,7}$]dec-4-ylidene]-N-1,3-benzodioxol-5-ylacetamide

The fumarate salt of the title compound was prepared as described in Example 13B, substituting Example 18A for Example 13A. ¹H NMR (methanol-d₄, 300 MHz) δ 2.04-2.09 (m, 2H), 2.19-2.33 (m, 3H), 2.67 (s, 1H), 3.41-3.47 (m, 2H), 3.56-3.65 (m, 4H), 4.44 (s, 1H), 5.92 (s, 2H), 5.96 (s, 1H), 6.66 (s, 1H; C₄H₄O₄), 6.75 (d, J=8.48 Hz, 1H), 6.91 (dd, J=8.48, 2.03 Hz, 1H), 7.25 (d, J=2.03 Hz, 1H) ppm; MS (DCI/NH₃) m/z 313 (M+H)⁺; Anal. (C$_{18}$H$_{20}$N$_2$O.0.6C$_4$H$_4$O$_4$) C, H, N.

Example 19

2-[1-azatricyclo[3.3.1.1$^{3,7}$]dec-4-yl]-N-1-naphthylacetamide

Example 3B (53.5 mg, 0.15 mmol) was dissolved in methanol (5 mL). 10% palladium on carbon (10 mg) was added to the reaction under nitrogen. Hydrogen was then introduced via balloon. The reaction was stirred under a hydrogen atmosphere at ambient temperature for 16 hours. The reaction was filtered and concentrated. The product was triturated from diethyl ether/methanol 9:1 (5 mL) to afford the title compound as the hydrochloride salt. ¹H NMR (methanol-d₄, 300 MHz) δ 1.96-2.00 (m, 2H), 2.07-2.33 (m, 5H), 2.63-2.75 (m, 1H), 2.81-2.89 (m 2H), 3.47-3.79 (m, 6H), 7.46-7.62 (m, 4H), 7.79 (d, J=8.14 Hz, 1H), 7.88-7.99 (m, 2H), ppm; MS (DCI/NH₃) m/z 321 (M+H)⁺; Anal. (C$_{21}$H$_{24}$N$_2$O.1.2HCl.0.25H$_2$O)C, H, N, Cl.

Example 20

2-[1-azatricyclo[3.3.1.1$^{3,7}$]dec-4-yl]-N-phenylacetamide

The title compound was prepared as described in Example 19, substituting Example 2 for Example 3B to afford the title compound as the hydrochloride salt. ¹H NMR (methanol-d₄, 300 MHz) δ 1.90-1.94 (m, 2H), 2.11-2.22 (m, 6H), 2.53-2.57 (m, 1H), 2.62-2.70 (m, 2H), 3.41-3.70 (m, 6H), 7.07-7.12 (m, 1H), 7.28-7.33 (m, 2H), 7.53-7.55 (m, 2H) ppm; MS (DCI/NH₃) m/z 271 (M+H); Anal. (C$_{17}$H$_{22}$N$_2$O.HCl.0.3H$_2$O)C, H, N, Cl.

Example 21

(4r)-N-(4-chlorophenyl)-1-azatricyclo[3.3.1.1$^{3,7}$]decane-4-carboxamide

Example 21A (4r)-4-azaadamantan-4-carbonitrile

Azaadamantan-4-one (prepared as described in Becker, D. P., Flynn, D. L. Synthesis 1992, 1080-1082) (3.76 g, 24.9 mmol) and p-toluenesulfonylmethyl isocyanide (6.38 g, 32.3 mmol) were dissolved in a mixture of dimethoxyethane (87 mL) and ethanol (3.2 mL) and chilled to −78° C. To the reaction mixture was added potassium tert-butoxide (6.70 g, 59.7 mmol) over a period of 1 minute. The reaction mixture was then stirred at 25° C. for 5 hours and then at 40° C. for 0.5 hour. The reaction mixture was cooled to ambient temperature and filtered through a glass frit. The filtrate was concentrated and the residue was purified by silica gel chromatography (10% concentrated NH$_4$OH in CH$_3$CN, R$_f$=0.25) to afford the title compound. MS (DCI/NH$_3$) m/z 163 (M+H)$^+$.

Example 21B (4r)-1-azatricyclo[3.3.1.1$^{3,7}$]decane-4-carboxylic acid

Example 21A (136 mg, 0.84 mmol) was dissolved in a mixture of concentrated HCl (aqueous) (2 mL) and glacial acetic acid (2 mL). The reaction mixture was stirred in a sealed tube at 110° C. for 14 hours. The reaction mixture was cooled to ambient temperature, concentrated and azeotroped twice with toluene to afford the title compound as the HCl salt. MS (APCI) m/z 182 (M+H)$^+$.

Example 21C (4r)-N-(4-chlorophenyl)azaadamantan-4-carboxamide

Example 21B (35 mg, 0.16 mmol) was dissolved in pyridine (5 mL). 4-chloroaniline (22 mg, 0.18 mmol), N-hydroxybenzotriazole (30 mg, 0.22 mmol), 4-dimethylaminopyridine (7 mg, 0.06 mmol) and ethyl-3(3-dimethylamino)propyl carbodiimide-HCl salt (50 mg, 0.26 mmol) were added to the reaction mixture. The reaction was stirred at ambient temperature for 18 hours. The reaction mixture was filtered through filter paper. The filtrate was concentrated in vacuo. The residue was purified by preparative HPLC on a Waters Nova-Pak® HR C18 6 µm 60 Å Prep-Pak® cartridge column (40 mm×100 mm) using a gradient of 10% to 100% acetonitrile in 10 mM aqueous ammonium acetate over 12 minutes at a flow rate of 70 mL/minute to provide the free base of the title compound. The solid was dissolved in ether/methanol 10:1 (5 mL) and treated with fumaric acid (10 mg/mL solution in 10:1 ether/methanol). The precipitate was collected by filtration and dried under vacuum to afford the title compound as a fumarate salt. $^1$H NMR (300 MHz, MeOH-d$_4$) δ 1.91-2.01 (m, 2H), 2.18 (m, 1H), 2.32-2.41 (m, 2H), 2.62 (bs, 2H), 3.10 (s, 1H), 3.52-3.70 (m, 6H), 6.71 (s, 1H; C$_4$H$_4$O$_4$), 7.27-7.34 (m, 2H), 7.55-7.62 ppm (m, 2H); MS (APCI) 291 (M+H)$^+$.

Example 22

(4r)-N-2-naphthyl-1-azatricyclo[3.3.1.1$^{3,7}$]decane-4-carboxamide

The title compound was prepared as a fumarate salt as described in Example 21C, substituting 2-naphthylamine for 4-chloroaniline. $^1$H NMR (MeOH-d$_4$, 500 MHz) δ 2.08-2.15 (m, 2H), 2.19-2.31 (m, 3H), 2.55 (bs, 2H), 3.05 (bs, 1H), 3.48 (d, J=11.60 Hz, 2H), 3.56 (s, 2H), 4.09 (d, J=12.21 Hz, 2H), 6.72 (s, 2H; C$_4$H$_4$O$_4$), 7.39 (ddd, J=8.09, 6.87, 1.22 Hz, 1H), 7.45 (ddd, J=8.09, 6.87, 1.22 Hz, 1H), 7.56 (dd, J=8.85, 2.14 Hz, 1H), 7.74-7.83 (m, 3H), 8.23 ppm (d, J=1.83 Hz, 1H); MS (ESI) m/z 307 (M+H)$^+$.

Example 23

(4r)-N-quinolin-6-yl-1-azatricyclo[3.3.1.1$^{3,7}$]decane-4-carboxamide

The fumarate salt of the title compound was prepared as described in Example 21C, substituting 6-aminoquinoline for 4-chloroaniline. $^1$H NMR (MeOH-d$_4$, 400 MHz) δ 1.99 (d, J=13.20 Hz, 2H), 2.20 (bs, 1H), 2.43 (d, J=12.89 Hz, 2H), 2.67 (bs, 1H), 3.15 (s, 1H), 3.52-3.72 (m, 7H), 6.70 (s, 4H; C$_4$H$_4$O$_4$), 7.52 (dd, J=8.29, 4.30 Hz, 1H), 7.83 (dd, J=9.21, 2.45 Hz, 1H), 7.99 (d, J=9.21 Hz, 1H), 8.30 (d, J=7.98 Hz, 1H), 8.39 (d, J=2.45 Hz, 1H), 8.76 (dd, J=4.45, 1.69 Hz, 1H); MS (ESI) m/z 308 ppm (M+H)$^+$; Anal. (C$_{19}$H$_{21}$N$_3$O.2C$_4$H$_4$O$_4$.0.3 NH$_4$OAc) C, H, N.

Determination of Biological Activity

To determine the effectiveness of representative compounds of this invention as ligands for α7 NNRs, the compounds of the invention were evaluated according to the [$^3$H]-DPPB binding assay. To determine the effectiveness of representative compounds of this invention as ligands for α4β2 NNRs, the compounds of the invention were evaluated according to the [$^3$H]-cytisine binding assay, which were performed as described below.

[$^3$H]-Cytisine Binding

Binding to α4β2 NNRs subtype was determined according to the conditions which were modified from the procedures described in Pabreza L. A., Dhawan, S., Kellar K. J., [$^3$H]-Cytisine Binding to Nicotinic Cholinergic Receptors in Brain, Mol. Pharm. 39: 9-12, 1991. Membrane enriched fractions from rat brain minus cerebellum (ABS Inc., Wilmington, Del.) were slowly thawed at 4° C., washed and resuspended in 30 volumes of BSS-Tris buffer (120 mM NaCl/5 mM KCl/2 mM CaCl$_2$/2 mM MgCl$_2$/50 mM Tris-Cl, pH 7.4, 4° C.). Samples containing 100-200 µg of protein and 0.75 nM [$^3$H]-cytisine (30 C$_i$/mmol; Perkin Elmer/NEN Life Science Products, Boston, Mass.) were incubated in a final volume of 500 µL for 75 minutes at 4° C. Seven log-dilution concentrations of each compound were tested in duplicate. Non-specific binding was determined in the presence of 10 µM (−)-nicotine. Bound radioactivity was isolated by vacuum filtration onto prewetted glass fiber filter plates (Millipore, Bedford, Mass.) using a 96-well filtration apparatus (Packard Instruments, Meriden, Conn.) and were then rapidly rinsed with 2 mL of ice-cold BSS buffer (120 mM NaCl/5 mM KCl/2 mM CaCl$_2$/2 mM MgCl$_2$). Packard Microscint-20® scintillation cocktail (40 µL) was added to each well and radioactivity determined using a Packard Topcount® instrument. The IC$_{50}$ values were determined by nonlinear regression in Microsoft Excel® software. K$_i$ values were calculated from the IC$_{50}$s using the Cheng-Prusoff equation, where K$_i$=IC$_{50}$/(1+[Ligand]/K$_D$).

[$^3$H]-DPPB Binding

[$^3$H]-DPPB, [$^3$H]-(S,S)-2,2-dimethyl-5-(6-phenyl-pyridazin-3-yl)-5-aza-2-azonia-bicyclo[2.2.1]heptane iodide, binding to the α7 NNR subtype was determined using membrane enriched fractions from rat brain minus cerebellum or human cortex (ABS Inc., Wilmington, Del.) as described in Anderson, D. J.; Bunnelle, W.; Surber, B.; Du, J.; Surowy, C.; Tribollet, E.; Marguerat, A.; Bertrand, D.; Gopalakrishnan, M. J. Pharmacol. Exp. Ther. (2008), 324, 179-187, which is incorporated herein by reference. Briefly, pellets were thawed at 4° C., washed and resuspended with a Polytron at a setting of 7 in 30 volumes of BSS-Tris buffer (120 mM NaCl, 5 mM KCl, 2 mM $CaCl_2$, 2 mM $MgCl_2$, and 50 mM Tris-Cl, pH 7.4, 4° C.). Seven log-dilution concentrations of test compounds containing 100-200 µg of protein, and 0.5 nM [$^3$H]-DPPB (62.8 Ci/mmol; R46V, Abbott Labs) were incubated in a final volume of 500 µL for 75 minutes at 4° C. in duplicate. Nonspecific binding was determined in the presence of 10 µM methyllycaconitine. Bound radioactivity was collected on Millipore Multiscreen® harvest plates FB presoaked with 0.3% polyethyleneimine using a Packard cell harvester, washed with 2.5 mL ice-cold buffer, and radioactivity was determined using a Packard TopCount Microplate beta counter. $IC_{50}$ values were determined by nonlinear regression in Microsoft® Excel or Assay Explorer. $K_i$ values were calculated from the $IC_{50}$s using the Cheng-Prusoff equation, where $K_i=IC_{50}/(1+[Ligand]/K_D)$. [$^3$H]-DPPB was obtained according to the preparation procedures described below.

[Methyl-$^3$H]2,2-Dimethyl-5-(6-phenyl-pyridazin-3-yl)-5-aza-2-azonia-bicyclo[2.2.1]heptane iodide Preparation

[Methyl-$^3$H]2,2-dimethyl-5-(6-phenyl-pyridazin-3-yl)-5-aza-2-azonia-bicyclo[2.2.1]heptane; iodide used in the [$^3$H]-DPPB binding assay above was prepared according to the following procedures.

Step 1: Preparation of t-Butyl(S,S)-5-(6-Phenyl-pyridazin-3-yl)-2,5-diaza-bicyclo[2.2.1]heptane-2-carboxylate Triethylamine (20 mL) was added to a suspension of t-butyl(S,S)-2,5-diazabicyclo[2.2.1]heptane-2-carboxylate (3.43 g, 17.3 mmol, Aldrich Chemical Company) and 3-chloro-6-phenylpyridazine (3.30 g, 17.3 mmol, Aldrich Chemical Company) in toluene (50 mL) and the mixture was heated under nitrogen at 100° C. for 7 days. The dark mixture was cooled to room temperature, and the resulting precipitate was isolated by filtration, washed with toluene (15 mL) and dried under vacuum to provide the title compound as an off-white solid. The filtrate was concentrated and the residue was purified by column chromatography on silica gel, eluting with ethyl acetate, to provide additional product: MS (DCI/$NH_3$) m/z 353 $(M+H)^+$.

Step 2: Preparation of (S,S)-2-Methyl 5-(6-phenyl-pyridazin-3-yl)-2,5-diaza-bicyclo[2.2.1]heptane The product obtained from Step 1 (3.41 g, 9.7 mmol) was dissolved in formic acid (20 mL) and treated with formalin (37% by weight, 1.0 g, 12.3 mmol). The mixture was heated at 100° C. for 1 hour, and the brown solution was cooled to room temperature and concentrated under vacuum. The residue was purified by column chromatography on silica gel, eluting with $CH_2Cl_2$—$CH_3OH$—$NH_4OH$ (95:5:1) to provide the title compound: MS (DCI/$NH_3$) m/z 267 $(M+H)^+$.

Step 3: Preparation of [$^3$H]-(S,S)-2,2-Dimethyl-5-(6-phenyl-pyridazin-3-yl)-5-aza-2-azonia-bicyclo[2.2.1] heptane iodide ([$^3$H]-DPPB)

[$^3$H]Methyl iodide in toluene (250 mCi in 0.1 mL, 85 Ci/mmol, American Radiolabeled Chemicals, Inc.) was combined with a solution of the product obtained from Step 2 in dichloromethane (0.788 mg, 2.96 µmole in 0.45 mL). The vial was capped and the mixture was allowed to react overnight at room temperature. Methanol was added and the solvents were evaporated to give 42 mCi. The product was taken up in methanol for HPLC purification.

Step 4: Purification by High Performance Liquid Chromatography (HPLC)

About 7 mCi of [$^3$H]-DPPB was evaporated to dryness and the residue was dissolved in total about 4.5 mL acetonitrile:water:trifluoroacetic acid (15:85:0.1). Approximately 0.9 mL per injection were made onto a Phenomenex® Luna® C18(2) column (5 micron, 250 mm×4.6 mm ID) using an Agilent HPLC system. [$^3$H]-DPPB was eluted by a gradient mobile phase from 10% B to 20% B in 20 minutes where Mobile Phase A=0.1% trifluoroacetic acid in water and Mobile Phase B=0.1% trifluoroacetic acid in acetonitrile at a flow rate of approximately 1 mL/minute. Peak detection and chromatograms were obtained with an Agilent variable wavelength UV detector set at 275 nm. The fractions containing [$^3$H]-DPPB were collected at approximately 14 minutes using an Agilent fraction collector. The fractions were combined and the solvents were evaporated in vacuo. The residue was dissolved in 200 proof ethanol (2 mL) to give 0.7 mCi.

Step 5: Determination of Purity and Specific Activity

[$^3$H]-DPPB was assayed using an Agilent 1100 series HPLC system consisting of a quaternary pump, an autosampler, and a photodiode array UV detector. A Packard Radiomatic A 500 radioactivity detector was connected to the HPLC system. For radiodetection, a 500 µL flow cell and a 3:1 ratio of Ultima-Flo M scintillation cocktail to HPLC mobile phase were used. The analyses were performed using a Phenomenex® Luna® C18(2) column (5 microns, 250 mm×4.6 mm ID). The mobile phase consisted of a gradient starting with 10% B and ramping to 20% B in 20 minutes followed by ramping to 90% B in 1 minute and hold at 90% B for 9 minutes, where Mobile Phase A=0.1% trifluoroacetic acid in water and Mobile Phase B=0.1% trifluoroacetic acid in acetonitrile. The flow rate was set at approximately 1 mL/min and the UV detection was set at 275 nm.

Compounds of the invention typically exhibited binding values ($K_i$) below 10 micromolar in one or both of these assays ([$^3$H]-Cytisine or [$^3$H]-DPPB binding). Preferred compounds had $K_i$ values ranging from 0.01 nanomolar to 100 nanomolar in one or both binding assays.

Compounds of the invention are ligands at α4β2, α7 NNRs, or both α4β2 and α7 NNRs that modulate function of α4β2, α7 NNRs, or both α4β2 and α7 NNRs by altering the activity of the receptor or signaling. The compounds can be inverse agonists that inhibit the basal activity of the receptor or antagonists that completely block the action of receptor-activating agonists. The compounds also can be partial agonists that partially block or partially activate the α4β2, α7, or both α4β2 and α7 NNR receptor or agonists that activate the receptor. Binding to α4β2, α7, or both α4β2 and α7 receptors also trigger key signaling processes involving various kinases and phosphatases and protein-protein interactions that are important to effects on memory, cytoprotection, gene transcription and disease modification.

Compounds of the invention can exist in radiolabeled form containing one or more atoms having an atomic mass or mass number different from the atomic mass or mass number most abundantly found in nature. Radioisotopes of atoms such as hydrogen, carbon, phosphorous, sulfur, flourine, chlorine, and iodine include, but are not limited to, $^3$H, $^{14}$C, $^{32}$P, $^{35}$S, $^{18}$F, $^{36}$Cl, and $^{125}$I, respectively. Compounds that contain other radioisotopes of these and/or other atoms are within the scope of this invention. Compounds containing tritium ($^3$H) and $^{14}$C radioisotopes are preferred in general for their ease in preparation and detectability. Radiolabled compounds of this invention can be prepared by the general methods well known to persons having ordinary skill in the art. Such radiolabeled compounds can be conveniently prepared by carrying out the procedures disclosed in the above Examples and Schemes by submitting a readily available radiolabeled reagent for a non-radiolabeled reagent. The radiolabeled compounds of the invention may be used as standards to determine the effectiveness of α7 NNR ligands in binding assays such as the assays described above.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of formula (I)

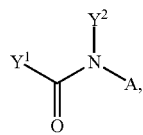

(I)

wherein
Y$^1$ is

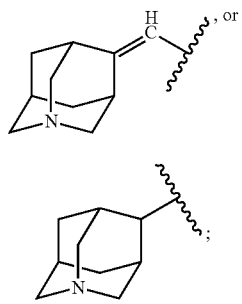

A is aryl, heteroaryl, cycloalkyl, cycloalkenyl, arylalkyl, heteroarylalkyl, heterocyclealkyl, cycloalkylalkyl, or cycloalkenylalkyl wherein the aryl, heteroaryl, cycloalkyl, cycloalkenyl, the aryl moiety of arylalkyl, the heteroaryl moiety of the heteroarylalkyl, the heterocycle moiety of the heterocyclealkyl, the cycloalkyl moiety of the cycloalkylalkyl, and the cycloalkenyl moiety of the cycloalkenylalkyl are each independently unsubstituted or substituted, wherein if A is a bicyclic aryl or bicyclic heteroaryl, the bicyclic aryl or bicyclic heteroaryl is selected from the group consisting of dihydroindenyl, indenyl, naphthyl, dihydronaphthalenyl, tetrahydronaphthalenyl, and quinolin; and
Y$^2$ is hydrogen or alkyl,
or a pharmaceutically acceptable salt thereof.

2. The compound of claim 1 wherein Y$^2$ is hydrogen, or a pharmaceutically acceptable salt thereof.

3. The compound according to claim 1, wherein Y$^1$ is formula (b), or a pharmaceutically acceptable salt thereof.

4. The compound of claim 3, wherein Y$^2$ is hydrogen, or a pharmaceutically acceptable salt thereof.

5. The compound according to claim 1, wherein Y$^1$ is (c), or a pharmaceutically acceptable salt thereof.

6. The compound of claim 5, wherein Y$^2$ is hydrogen, or a pharmaceutically acceptable salt thereof.

7. A compound selected from the group consisting of
2-[1-azatricyclo[3.3.1.1$^{3,7}$]dec-4-ylidene]-N-(4-methylphenyl)acetamide;
2-[1-azatricyclo[3.3.1.1$^{3,7}$]dec-4-ylidene]-N-phenylacetamide;
2-[1-azatricyclo[3.3.1.1$^{3,7}$]dec-4-ylidene]-N-1-naphthylacetamide;
2-[1-azatricyclo[3.3.1.1$^{3,7}$]dec-4-ylidene]-N-(3-chlorophenyl)acetamide;
2-[1-azatricyclo[3.3.1.1$^{3,7}$]dec-4-ylidene]-N-(4-tert-butylphenyl)acetamide;
2-[1-azatricyclo[3.3.1.1$^{3,7}$]dec-4-ylidene]-N-[4-(trifluoromethoxy)phenyl]acetamide;
2-[1-azatricyclo[3.3.1.1$^{3,7}$]dec-4-ylidene]-N-[4-(trifluoromethyl)phenyl]acetamide;
2-[1-azatricyclo[3.3.1.1$^{3,7}$]dec-4-ylidene]-N-(4-chloro-1-naphthyl)acetamide;
2-[1-azatricyclo[3.3.1.1$^{3,7}$]dec-4-ylidene]-N-(4-bromophenyl)acetamide;
2-[1-azatricyclo[3.3.1.1$^{3,7}$]dec-4-ylidene]-N-pyridin-3-ylacetamide;
2-[-1-azatricyclo[3.3.1.1$^{3,7}$]dec-4-ylidene]-N-pyridin-2-ylacetamide;
2-[1-azatricyclo[3.3.1.1$^{3,7}$]dec-4-ylidene]-N-quinolin-6-ylacetamide;
2-[1-azatricyclo[3.3.1.1$^{3,7}$]dec-4-ylidene]-N-(4-chlorophenyl)acetamide;
2-[1-azatricyclo[3.3.1.1$^{3,7}$]dec-4-ylidene]-N2-naphthylacetamide;
2-[1-azatricyclo[3.3.1.1$^{3,7}$]dec-4-ylidene]-N-(4-chlorobenzyl)acetamide;
2-[1-azatricyclo[3.3.1.1$^{3,7}$]dec-4-ylidene]-N-1,1'-biphenyl-4-ylacetamide;
2-[1-azatricyclo[3.3.1.1$^{3,7}$]dec-4-ylidene]-N-(4-fluorophenyl)acetamide;
(4r)-N-(4-chlorophenyl)-1-azatricyclo[3.3.1.1$^{3,7}$]decane-4-carboxamide;
(4r)-N-2-naphthyl-1-azatricyclo[3.3.1.1$^{3,7}$]decane-4-carboxamide; and
(4r)-N-quinolin-6-yl-1-azatricyclo[3.3.1.1$^{3,7}$]decane-4-carboxamide;
or a pharmaceutically acceptable salt thereof.

8. A pharmaceutical composition comprising a therapeutically effective amount of the compound of claim 1, or a pharmaceutically acceptable salt thereof, in combination with one or more pharmaceutically acceptable carriers.

9. The pharmaceutical composition of claim 8 further comprising one or more atypical antipsychotics.

* * * * *